(12) United States Patent
Sawamoto et al.

(10) Patent No.: US 7,423,435 B2
(45) Date of Patent: Sep. 9, 2008

(54) METHOD AND APPARATUS FOR MEASURING GRAMMAGE

(75) Inventors: Hidetada Sawamoto, Hyogo (JP); Shinichi Nagata, Hyogo (JP)

(73) Assignee: Oji Paper Co., Ltd., Tokyo (JP)

( * ) Notice: Subject to any disclaimer, the term of this patent is extended or adjusted under 35 U.S.C. 154(b) by 0 days.

(21) Appl. No.: 11/451,490

(22) Filed: Jun. 13, 2006

(65) Prior Publication Data

US 2006/0288782 A1    Dec. 28, 2006

(30) Foreign Application Priority Data

Jun. 14, 2005  (JP)  .............................. 2005-174197

(51) Int. Cl.
*G01R 27/32*   (2006.01)
*G01R 29/12*   (2006.01)
*G01R 27/04*   (2006.01)

(52) U.S. Cl. ...................... 324/644; 324/458; 324/633; 324/640; 324/643

(58) Field of Classification Search ................. 324/664, 324/671, 689, 694, 708, 716, 336–343; 343/785
See application file for complete search history.

(56) References Cited

U.S. PATENT DOCUMENTS

| | | | |
|---|---|---|---|
| 3,828,270 A * | 8/1974 | Ebisch ............... | 330/130 |
| 4,033,882 A * | 7/1977 | Fletcher et al. ........ | 398/204 |
| 5,826,458 A * | 10/1998 | Little ................ | 73/73 |
| 6,009,317 A * | 12/1999 | Wynn ................ | 455/296 |
| 7,151,380 B2 * | 12/2006 | Typpo et al. .......... | 324/643 |
| 2001/0000946 A1 * | 5/2001 | Moeller et al. ........ | 324/640 |

FOREIGN PATENT DOCUMENTS

| | | | |
|---|---|---|---|
| EP | 0 547 968 A | * | 6/1993 |
| JP | 02 272349 A | * | 11/1990 |
| JP | 02272349 | * | 11/1990 |
| JP | 0 547 968 A | | 6/1993 |
| JP | 2003-254915 | * | 9/2003 |
| JP | 2003254915 | * | 9/2003 |

OTHER PUBLICATIONS

R.J.King: "On-line Industrial Applications of Microwave Moisture Sensors" Sensors Update, vol. 7, 2000, pp. 109 to 170.*

(Continued)

*Primary Examiner*—Vincent Q. Nguyen
*Assistant Examiner*—Benjamin M Baldridge
(74) *Attorney, Agent, or Firm*—Edwards Angell Palmer & Dodge LLP

(57) ABSTRACT

A grammage measuring apparatus including a dielectric resonator which is arranged only at one side surface of a sample; a shielding container with which the dielectric resonator is substantially covered except for a sample measuring surface; a microwave excitation device which causes the dielectric resonator to generate an electric field vector; a detection device which detects transmission energy or reflection energy by the dielectric resonator; a storage device in which a calibration curve indicating a resonance frequency shift amount for a grammage is stored; and a data processing device which calculates the grammage of a measuring sample from the calibration curve and measurement result of the resonance frequency shift amount of the measuring sample.

16 Claims, 21 Drawing Sheets

OTHER PUBLICATIONS

Knochel R: "Technology and Signal Processing of Dielectrometric Microwave Sensors for Industrial Applications", Transactions of the Metal Finishers Association of India, XX, IN, vol. 7, 2000, pp. 65 to 105.*

R.J. KIng, "On-line Industrial Applications of Microwave Moisture Sensors", Sensors Update, vol. 7, 2000, pp. 109-170.*

Thorsten Hauschild, "Density and Moisture Measurements Using Mcirowave Resonators", Electromagenetic Aquametry, 2005, pp. 193-215.*

Thorsten Hauschild: "Density and Moisture Measurements Using Microwave Resonators", Electromagnetic Aquametry, 2005, pp. 193 to 215.

Knöchel R: "Technology and Signal Processing of Dielectrometric Microwave Sensors for Industrial Applications", Transactions of the Metal Finishers Association of India, XX, IN, vol. 7, 2000, pp. 65 to 105.

* cited by examiner

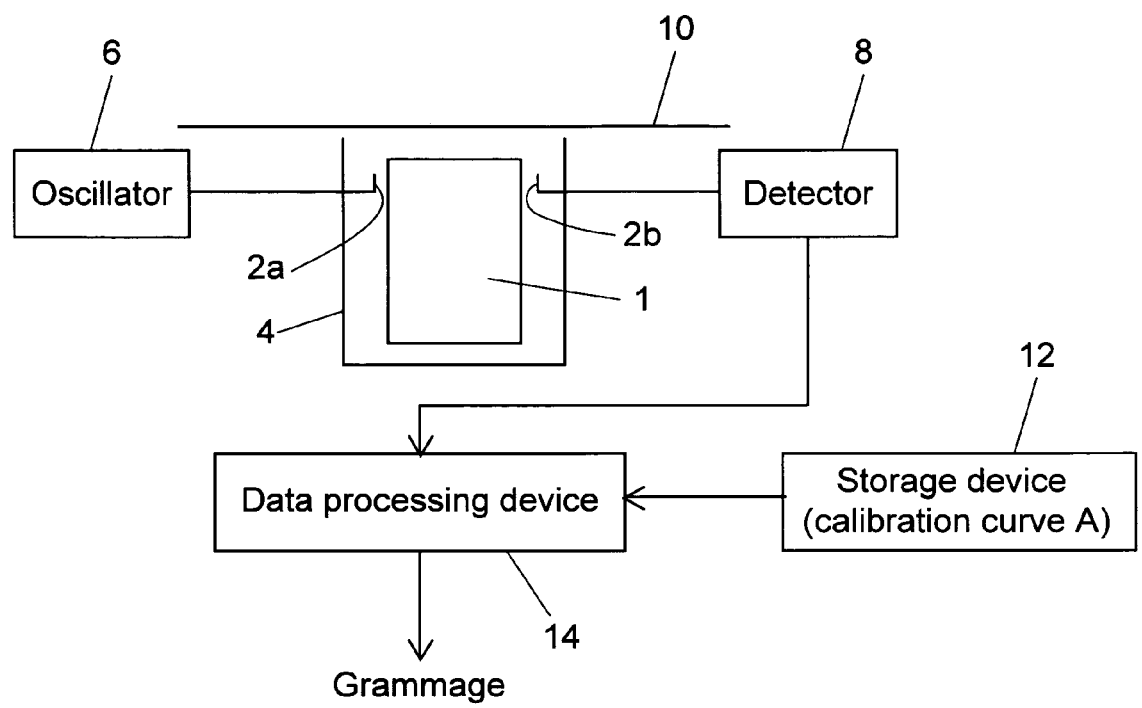

7-Bit TTL signal (From Personal Computer)

From Microwave Sweeper Oscillator → $P_{IN}$ → [box] → $P_{OUT}$ →

$$\text{Attenuation (dB)} = -10\log_{10}(P_{out}/P_{in})$$

| 7-Bit signal | Attenuation |
|---|---|
| 0000001 | 0.125 |
| 0000010 | 0.250 |
| 0000100 | 0.500 |
| 0001000 | 1.000 |
| 0010000 | 2.000 |
| 0100000 | 4.000 |
| 1000000 | 8.000 |

⬇ Several second later

METHOD AND APPARATUS FOR MEASURING GRAMMAGE

BACKGROUND OF THE INVENTION

1. Field of the Invention

The present invention relates to a method and an apparatus for measuring a thickness or grammage (mass per 1 m²) of a sheet-like substance including paper, non-woven fabric, and film by utilizing resonance of a microwave.

2. Description of the Related Art

The thickness and the grammage of the sheet-like substance including paper and film are one of the most important characteristics in product quality of a production process. In the production process, it is necessary to perform online measurements of the thickness, particularly the grammage in a case of the paper.

Conventionally, a method in which a beta ray is utilized has been used as the method of performing the online measurements of the grammage in producing the paper, and particularly, krypton-85 is mainly used. The beta ray is a kind of radiation and is a charged particle generated by beta decay of a radioactive isotope. One of the surfaces of a sample is radiated with the beta ray, and an amount of beta ray transmitted through the sample is detected at the other surface. The beta ray with which one of the surfaces of the sample is radiated, excites states of atoms constituting the sample, or ionizes the atoms in the course of the beta ray through the sample. The beta ray also experiences energy loss by losing kinetic energy of the beta ray in itself, and then the beta ray is transmitted through the other surface. The amount of energy loss is determined by physical properties, such as an absorption coefficient, and an amount such as a thickness and a grammage, of a substance constituting the sample. The energy loss is expressed by Formula (3).

$$I = I_0 \exp(-\mu\rho\chi) \qquad (3)$$

where, $I_0$: radiated radiation intensity $I$: post-transmission radiation intensity $\mu$: absorption coefficient determined by radiation energy and sample $\rho$: density of sample $\chi$: thickness of transmission substance Because of $b = \rho \cdot \chi$ when the grammage is expressed by "b", Formula (3) can be expressed by Formula (4).

$$I = I_0 \exp(-\mu b) \qquad (4)$$

That is, the absorption coefficient $\mu$ which is determined in each sample can be determined by computation, when a calibration curve is previously made in each sample which is of a measuring target using a standard sample whose grammage is known. Therefore, during the operation, the grammage of the sample can be determined from Formula (4) by measuring the radiated radiation intensity $I_0$ and the post-transmission radiation intensity $I$. Thus, in the method in which the beta ray is utilized, although it is necessary to previously determine the absorption coefficient of the target sample, the grammage can instantly be determined online during the operation, so that a paper machine can be controlled online.

SUMMARY OF THE INVENTION

However, in a case of the method in which the beta ray is utilized for the grammage measurements, the beta ray is harmful to the human body because the beta ray is radiation. Therefore, the beta ray is difficult to handle. In the event that an unexpected contingency is generated, the operator might be affected by the beta ray.

In view of the foregoing, an object of the invention is to provide a grammage measuring apparatus, which is inexpensive and easy to handle, and a grammage measuring method thereof.

The grammage measuring method of the invention is to determine a grammage of a measuring sample by arranging a sample measuring surface of a dielectric resonator only at one surface side of a sample under a fixed condition.

One aspect of the grammage measuring method comprises the steps of a first step of obtaining a calibration curve, which indicates a resonance frequency shift amount for a grammage, by measuring a resonance frequency shift amount of the dielectric resonator for each grammage of a standard sample, which has a known grammage, by changing the grammage while a dielectric constant and a density of the standard sample are kept constant;

a second step of measuring a resonance frequency shift amount of a measuring sample, which has the same dielectric constant and density as the standard sample and has an unknown grammage, under the fixed condition with the dielectric resonator; and a third step of determining the grammage of the measuring sample from the measuring value of the second step and the calibration curve.

The resonance frequency shift amount is a difference in resonance frequency between absence and presence of the sample (the standard sample or the measuring sample).

Another aspect of the grammage measuring method comprises the steps of:

a step of calculating a constant "A" according to the following equation (1) by measuring a resonance frequency shift amount $\Delta f$ of a standard sample, which has a known grammage "b", under the fixed condition; and a step of calculating a grammage "b" of the measuring sample, which has the same dielectric constant and density as the standard sample, according to the following equation (5) by measuring a resonance frequency shift amount $\Delta f$ of the measuring sample under the fixed condition with the dielectric resonator.

$$\Delta f = A \cdot b \qquad (5)$$

where $\Delta f = f_0 - f_S$, $f_0$: a resonance frequency in a case where the sample (standard sample or measuring sample) is absent, and $f_S$: a resonance frequency in a case where the sample (standard sample or measuring sample) is present.

In the grammage measuring method of the invention, the fixed condition may be to perform the measurements by bringing the sample into contact with the sample measuring surface of the dielectric resonator, or the fixed condition may be to perform the measurements by separating the sample away from the sample measuring surface of the dielectric resonator by a predetermined distance.

In the grammage measuring method of the invention, a moisture content amount or a moisture content ratio of the sample may also be determined based on a difference in resonance peak level between the absence and presence of the sample.

FIG. 1 shows a grammage measuring apparatus according to the invention.

One aspect of the grammage measuring apparatus of the invention includes a dielectric resonator 1 which is arranged only at one surface side of a sample 10; a shielding container 4 with which the dielectric resonator 1 is substantially covered with the exception of a sample measuring surface; a microwave excitation device 6 and 2a which causes the dielectric resonator 1 to generate an electric field vector; a detection device 8 and 2b which detects transmission energy or reflection energy by the dielectric resonator 1; a storage device 12 in which a calibration curve is stored, the calibration curve indicating a resonance frequency shift amount for a grammage, the calibration curve being produced based on the resonance frequency shift amount, the resonance frequency shift amount for each grammage being measured under a fixed condition with the dielectric resonator 1 by changing the grammage of a standard sample, a dielectric constant and density of the standard sample being kept constant, the grammage being known in the standard sample; and a data processing device 14 which computes the grammage of a measuring sample from the calibration curve and measurement result of the resonance frequency shift amount of the measuring sample, the dielectric constant and the density of the measuring sample being equal to those of the standard sample. The microwave excitation device includes a microwave oscillator 6 and an antenna 2a, and the detection device includes a wave detector 8 and an antenna 2b.

Another aspect of the grammage measuring apparatus of the invention includes the dielectric resonator 1, the shielding container 4, the microwave excitation device 6 and 2a, and the detection device 8 and 2b. However, in this aspect, the storage device 12 stores a constant "A" of the following equation (6). The constant "A" is determined based on a resonance frequency shift amount $\Delta f$ for each grammage measured under the fixed condition with the dielectric resonator 1 by changing a grammage "b" of a standard sample which has a known grammage "b". Furthermore, the data processing device 14 calculates a grammage "b" of a measuring sample, which has the same dielectric constant and density as the standard sample, according to the following equation (6) from the constant "A" stored in the storage device 12 and the measurement result of the resonance frequency shift amount $\Delta f$ of the measuring sample under the fixed condition with the dielectric resonator.

$$\Delta f = A \cdot b \quad (6)$$

where $\Delta f = f_0 - f_S$, $f_0$: a resonance frequency in a case where the sample (standard sample or measuring sample) is absent, and $f_S$: a resonance frequency in a case where the sample (standard sample or measuring sample) is present.

In the grammage measuring apparatus of the invention, the data processing device 14 may have a function of determining a moisture content amount or a moisture content ratio of the sample based on a difference in resonance peak levels between the absence and presence of the sample, and thereby the grammage measuring apparatus may have a moisture measuring function.

The grammage measuring apparatus of the invention may include an orientation measuring function. In one mode of the grammage measuring apparatus including the orientation measuring function, the dielectric resonator includes a plurality of dielectric resonators arranged in a same first plane, and the dielectric resonators are arranged so that their electric field vectors having one-directional components in a second plane within a sample, the second plane being parallel to the first plane, are different from one another, the data processing device 14 further has a function of determining a dielectric anisotropy of the sample based on a difference in output among the dielectric resonators, and thereby the grammage measuring apparatus has an orientation measuring function, and the calibration curve or the constant A is determined using an average value of the outputs of the plurality of dielectric resonators, and the grammage of the measuring sample is determined from the calibration curve or the constant A and measurement result based on the average value of the outputs of the plurality of dielectric resonators for the measuring sample.

In the grammage measuring apparatus of the invention, sometimes an amplifier circuit includes a time delay element, and the amplifier circuit being connected to each of the plurality of dielectric resonators to amplify output of each of the plurality of dielectric resonators. In a preferred mode, each of the plurality of dielectric resonators constitutes a dielectric resonator detection system including a variable electric signal attenuation and amplification means, the variable electric signal attenuation and amplification means being inserted between a microwave oscillator and a resonance peak level detection circuit, the microwave oscillator being connected to each of the plurality of dielectric resonators, the resonance peak level detection circuit being connected to the amplifier circuit to detect a resonance peak level from the output of the amplifier circuit, and the grammage measuring apparatus includes control means for comparing the output from the resonance peak level detection circuit of each dielectric resonator detection system to a predetermined target resonance peak level to generate a signal for changing attenuation or an amplification degree for the variable electric signal attenuation and amplification means so that the output from the resonance peak level detection circuit is brought close to the predetermined target resonance peak level.

The dielectric resonator detection system further includes an analog/digital conversion circuit unit, and the predetermined target resonance peak level voltage can be set within an input range of the analog/digital conversion circuit unit.

An example of the variable electric signal attenuation and amplification means is a programmable attenuator. The programmable attenuator can be connected between the dielectric resonator and the microwave oscillator. Another example of the variable electric signal attenuation and amplification means is one which is provided in the amplifier circuit In another mode of the grammage measuring apparatus including the orientation measuring function, the dielectric resonator includes a single dielectric resonator, and the dielectric resonator has a one-directional component in a second plane within a sample, the second plane being parallel to the first plane, the grammage measuring apparatus has a rotating mechanism which rotates the sample or the dielectric resonator in the plane parallel to the plane, the data processing device 14 has a function of determining a dielectric anisotropy of the sample from a difference in dielectric resonator output according to the rotation of the rotating mechanism, and thereby the grammage measuring apparatus has an orientation measuring function, and the calibration curve or the constant "A" is determined using an average value of the dielectric resonator outputs according to the rotation of the rotating mechanism, and the grammage of the measuring sample is determined from the calibration curve or the constant "A" and measurement result based on the average value of the dielectric resonator outputs for the measuring sample.

Thus, in the invention, the resonance frequency shift amount of the measuring sample is measured with the dielectric resonator, and the measurement value of the resonance frequency shift amount is applied to the previously determined calibration curve to determine the grammage of the sample, or the constant "A" is previously determined to obtain the grammage of the sample using the equation. Therefore, the grammage can safely be measured with ease of handling while the radiation and the like having the harmful influence on the human body are not utilized.

BRIEF DESCRIPTION OF THE DRAWINGS

FIG. 1 is a block diagram schematically showing a grammage measuring apparatus according to the invention;

FIG. 22 is a view in which output voltage of each dielectric resonator is displayed on a display.

DESCRIPTION OF THE PREFERRED EMBODIMENTS

Figure 2A:
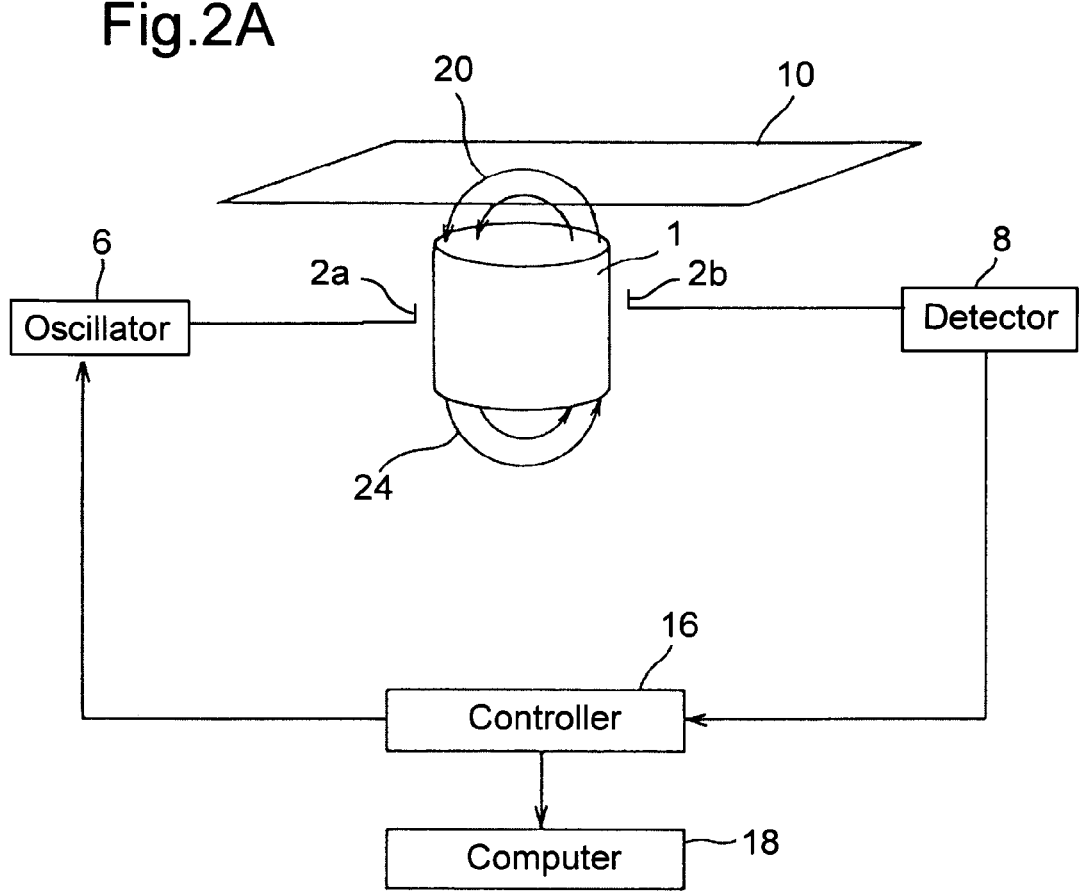
FIG. 2A is a block diagram schematically showing a dielectric resonator in the invention.
Figure 2B:
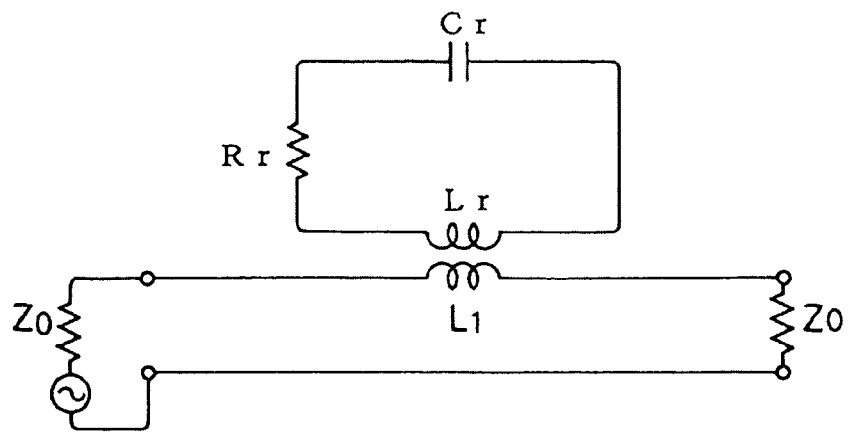
FIG. 2B shows an equivalent circuit thereof.

FIGS. 2A and 2B schematically show a preferred embodiment of the invention. FIG. 2A is a block diagram showing a dielectric resonator, and FIG. 2B is an equivalent circuit thereof.

A resonance mode, in which a dielectric resonator 1 is resonated while an electric field vector 20 exuding to the outside from the dielectric resonator 1 exists, can be generated by arranging microwave rod antennas 2a and 2b at proper positions and orientations with respect to the dielectric resonator 1. In FIG. 2A, a shielding container is omitted for convenience. Examples of the resonance mode include a HEM mode in a case where a sample surface facing the dielectric resonator 1 is formed in a circular shape and a TM mode and a TE mode in a case where the sample surface is formed in a square shape. The intensity of the electric field vector 20 is substantially exponentially declined with a distance from the dielectric resonator 1. However, when a sample 10 is placed while slightly separated away from the dielectric resonator 1, or when the sample 10 is placed while being in contact with the dielectric resonator 1, a resonance frequency is shifted according to a dielectric constant of the sample 1 by electromagnetic coupling.

A microwave emitted from an oscillator 6 is electromagnetically coupled to the dielectric resonator 1 by the rod antenna 2a, and the dielectric resonator 1 can be brought into a resonant state. The electric field vector 20 of the dielectric resonator 1 emerges in substantially parallel with the surface of the sample 10, which generates interaction with dipole moment possessed by the sample 10. The transmitted microwave from the dielectric resonator 1 is detected through the rod antenna 2b by a wave detector 8. A controller 16 captures microwave intensity detected by the wave detector 8. The numeral 18 designates a computer which is of a data processing device for determining the grammage from the detected microwave intensity.

Figure 3A:
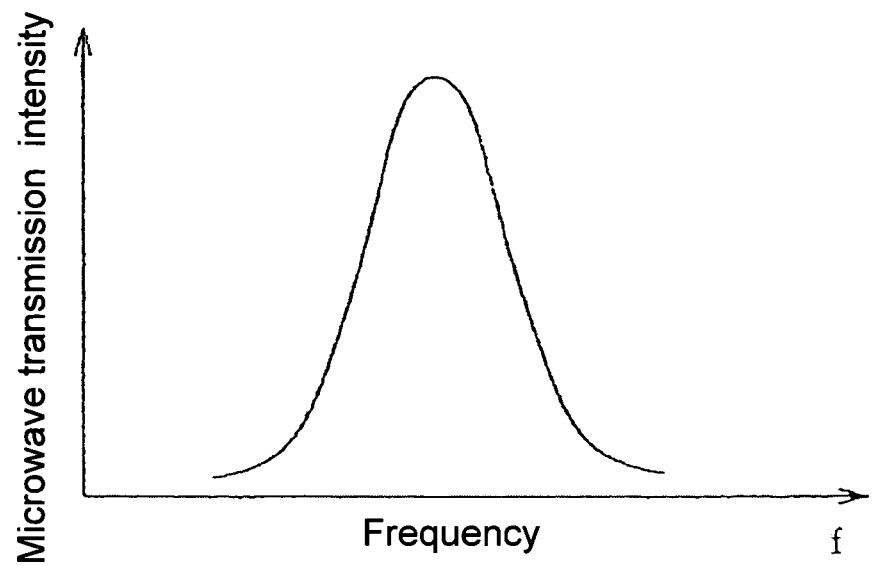
FIG. 3A shows a waveform exhibiting a resonance peak in the dielectric resonator.

Next, a principle of grammage (thickness) measurement will be described. In the dielectric resonator 1, there is a relationship shown in FIG. 3A between the transmitted microwave intensity and the frequency. The resonance curve shown in FIG. 3A is called a Q curve. The Q curve is changed according to Formula (7), when the sample 10 is placed.

$$\frac{\omega_S - \omega_0}{\omega_0} \cong \frac{1}{4\overline{W}} \int_{\Delta V} \left[ \left( P + \frac{J}{j\omega_a} \right) \cdot E_a^* + \mu_0 M \cdot H_a^* \right] dv \quad \text{[Formula (7)]}$$

$$\overline{W} = \frac{1}{2} \int_V \varepsilon_S |E_a|^2 dv$$

$$\omega = 2\pi f$$

$\omega_S$: complex angular frequency (in a case where sample is present)

$\omega_0$: complex angular frequency (in a case where sample is absent)

P: electric polarization

J: conduction current density $E_a$: electric field

M: magnetic field $\varepsilon_S$: dielectric constant of dielectric resonator

*: indicating a complex number
Ha: magnetization
$\mu_o$: magnetic permeability

Figure 3B:
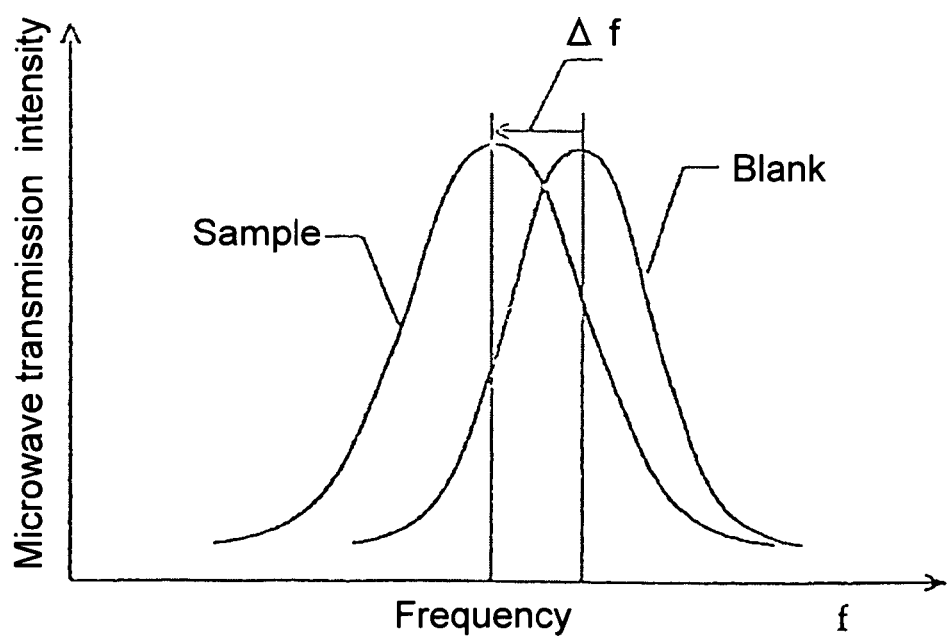
FIG. 3B shows waveforms exhibiting a change in resonance curve according to presence or absence of a sample.

FIG. 3B shows the change in resonance frequency according to the presence or absence (blank) of the sample.

Although Formula (7) is originally reached in a case of a cavity resonator, because the sample is substantially arranged near the dielectric resonator 1 or brought into contact with the dielectric resonator 1, Formula (7) is also reached in the invention.

In Formula (7), the sign W designates accumulation energy in the dielectric resonator 1, and the accumulation energy W is determined by the dielectric constant of dielectric resonator $\epsilon_S$ and the electric field $E_a$. Therefore, the accumulation energy W is an intrinsic value of the apparatus which is not affected by the sample to be measured. Then, a term of $\mu_0 \cdot M \cdot Ha^*$ becomes zero because the sample is a nonmagnetic dielectric material. Formula (8) is obtained by summarizing and rewriting Formula (7).

$$\frac{\omega_S - \omega_0}{\omega_0} \cong \frac{1}{4\overline{W}} \int_{\Delta V} \left[ \left( P + \frac{J}{j\omega_a} \right) \cdot E_a^* \right] dv \quad \text{[Formula (8)]}$$

The complex dielectric constant is divided into a real part and an imaginary part, and only the real part, namely, only a dielectric constant $\epsilon'$ is described to obtain Formula (9).

$$\frac{\omega_S - \omega_0}{\omega_0} \cong \frac{1}{4\overline{W}} \int_{\Delta V} \varepsilon_0 (\varepsilon' - 1) E_a^2 dv \quad \text{[Formula (9)]}$$

When an integrating term on the right side is integrated, Formula (10) is obtained.

$$\frac{\omega_S - \omega_0}{\omega_0} \cong \frac{\varepsilon_0 (\varepsilon' - 1) E_a^2 \cdot \Delta V}{4\overline{W}} \quad \text{[Formula (10)]}$$

$\Delta V$ is a volume of the sample, and $\Delta V$ is expressed by $\Delta V = S \cdot d$. Where "S" is a measuring area of the sample, and "d" is a thickness of the sample. When $\Delta V = S \cdot d$ is substituted for Formula (10), Formula (11) is obtained.

$$\frac{\omega_S - \omega_0}{\omega_0} \cong -\frac{\varepsilon_0 (\varepsilon' - 1) E_a^2 \cdot S}{4\overline{W}} \cdot d \quad \text{[Formula (11)]}$$

Because of $\omega = 2\pi f$, $\omega = 2\pi f$ is substituted for Formula (11), Formula (12) is obtained.

$$\frac{2\pi (f_S - f_0)}{2\pi f_0} \cong -\frac{\varepsilon_0 (\varepsilon' - 1) E_a^2 \cdot S}{4\overline{W}} \cdot d \quad \text{[Formula (12)]}$$

When $2\pi$ on the left side are eliminated to multiply $-fa$, Formula (13) is obtained.

$$f_0 - f_S \cong \frac{f_a \varepsilon_0 (\varepsilon' - 1) E_a^2 \cdot S}{4\overline{W}} \cdot d \quad \text{[Formula (13)]}$$

Because the grammage "b" is expressed by $b = e \cdot d$ using density "e" and the thickness "d" of the sample, Formula (14) is obtained when $b = e \cdot d$ is substituted for Formula (13).

$$f_0 - f_S \cong \frac{f_0 \varepsilon_0 (\varepsilon' - 1) E_a^2 \cdot S}{4\overline{W} \cdot e} \cdot b \quad \text{[Formula (14)]}$$

Each of $f_0$, $E_a$, W, and S is an intrinsic constant of the apparatus, $\epsilon_0$ is a constant, and $\epsilon'$ is the sample dielectric constant which is determined by the sample. Therefore, when the constant portions are summarized, Formula (15) is obtained.

$$\Delta f = A \cdot b \quad \text{[Formula (15)]}$$

where, $\Delta f = f_0 - f_S$
$f_0$: resonance frequency in a case where sample is absent
$f_s$: resonance frequency in a case where sample is present
A: constant That is, the resonance frequency shift amount $\Delta f$ shown in FIG. 3B is proportional to the grammage "b" of the sample. When the constant "A" is previously determined, the thickness of the sample can be obtained by measuring $\Delta f$.

A procedure of determining the constant "A" will specifically be described below. In the actual sheet making, for the same kind sheets of paper, a compounding ratio and the density of the materials are maintained constant while the grammage is varied. The sample dielectric constant is a value which is determined by the compounding ratio of the paper materials, the paper density, and the moisture content The materials include pulp, pigment, and chemicals which are added according to the intended use. The kind of paper is determined by the materials, and the compounding ratio of the paper is also determined, as described above. For example, the pulp material is determined in each kind of paper. That is, for the same kinds of sheets of paper having different grammages, the dielectric constant is maintained constant because a calender condition and the like are determined so that not only the compounding ratio is maintained constant but also the density is maintained constant. The grammage is controlled by adjustment of the material amount in sheet making. Specifically, when producing paper with larger grammage, the material amount is increased, and when producing paper with smaller grammage, the material amount is decreased. Thus, the constant "A" has the value determined by the same kind sheet of paper.

Figure 4:
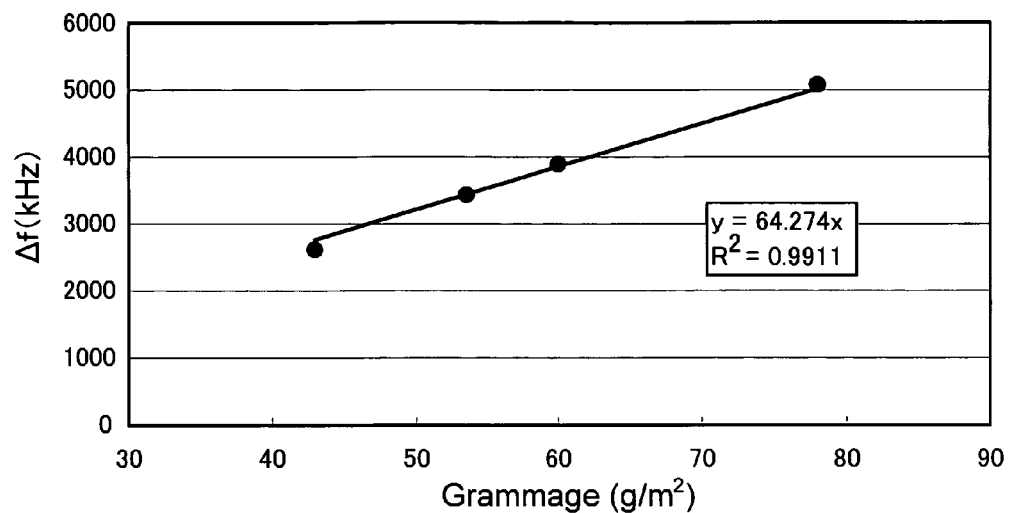
FIG. 4 is a graph showing a relationship between a grammage (displayed in $g/m^2$) and a resonance frequency shift amount.

Then, the grammage is changed while the material amount is adjusted in several stages, and the resonance frequency shift amount $\Delta f$ is recorded according to each stage. The grammages of the sheets of paper in which sheet making is finished are measured offline to plot the resonance frequency shift amount $\Delta f$ corresponding to each grammage in each stage. FIG. 4 shows an example of the relationship between the grammage and the resonance frequency shift amount $\Delta f$. As can be seen from FIG. 4, the grammage and the resonance frequency shift amount $\Delta f$ exhibit a linear correlation, and a slope of the linear correlation indicates the constant "A" of Formula (15).

In the invention, there are two modes, namely, a mode in which the correlation is maintained as a calibration curve and a mode in which the constant "A" determined from the correlation is maintained. In the mode in which the calibration curve is used, the resonance frequency shift amount $\Delta f$ measured for an unknown sample is applied to the calibration curve to determine the grammage. In the mode in which the constant "A" is used, $\Delta f$ measured for the unknown sample is applied to Formula (15), and the grammage is determined by calculation. When unknown paper is measured online in the above manner, the grammage of the unknown sample can immediately be obtained using Δf obtained by the measurement and the previously determined calibration curve or constant "A".

Thus, in the invention, the grammage is determined from the resonance frequency shift amount Δf, namely, from a peak frequency shift amount of the resonance curve, so that it is necessary to accurately measure a peak frequency. Sharpening the resonance curve by increasing resonance sharpness (Q value) is effective in the accurate measurements of the peak frequency. Therefore, the inventors obtain the following knowledge as a result of various experiments for a shape of dielectric resonator, a shape of the shielding container, a relationship therebetween, and the like.

It is preferable that the surroundings of the dielectric resonator be covered with a shielding material made of an electrically conductive material except for a sample measuring surface. This enables enhancement of the Q value of the resonance curve. At this point, more preferably the shielding material made of the electrically conductive material is also arranged in the sample measuring surface of the dielectric resonator to arrange the sample between the sample measuring surface of the dielectric resonator and the shielding material.

For the shape of the dielectric resonator, a cylindrical shape is more preferable than a prismatic shape in order to measure the grammage. When the cylindrical dielectric resonator is used, the electric field vector is distributed so as to draw a circle in a case where the resonance mode is a $TM_{01\delta}$ mode. Therefore, even if the sample has anisotropy in the dielectric constant, the constant measuring value is obtained irrespective of the sample orientation.

On the other hand, in the prismatic dielectric resonator, when a bottom surface of the prism is set at the sample measuring surface, the electric field vector becomes parallel to the sample measuring surface due to the shape of the prismatic dielectric resonator. For example, when the sample having the anisotropy in the dielectric constant is measured, the measuring value is changed by the orientation of the sample in almost all of the TM modes such as $TM_{101}$ and $TM_{201}$. Although the change in measuring value by the orientation of the sample is suitable to the purpose of the anisotropy measurements of sample dielectric constant as described later, the change in measuring value becomes a drawback for the grammage measurements which is of the main purpose of the invention. In one of the methods of measuring the sample having the dielectric constant anisotropy with the prismatic dielectric resonator, plural prismatic dielectric resonators are arranged, and pieces of data can simultaneously be obtained from the plural dielectric resonators to determine the grammage from an average of the pieces of data. In another method, one prismatic dielectric resonator is used, the prismatic dielectric resonator is rotated in a sample in-plane direction, and the pieces of data from the dielectric resonator can be obtained at plural points in the rotating direction to determine the grammage from the average of the pieces of data.

The method and apparatus of the invention also include a moisture measuring function where a data processing device has a function of determining the moisture content amount or moisture content ratio of the sample based on the difference in resonance peak levels between absence and presence of the sample.

Figure 5:
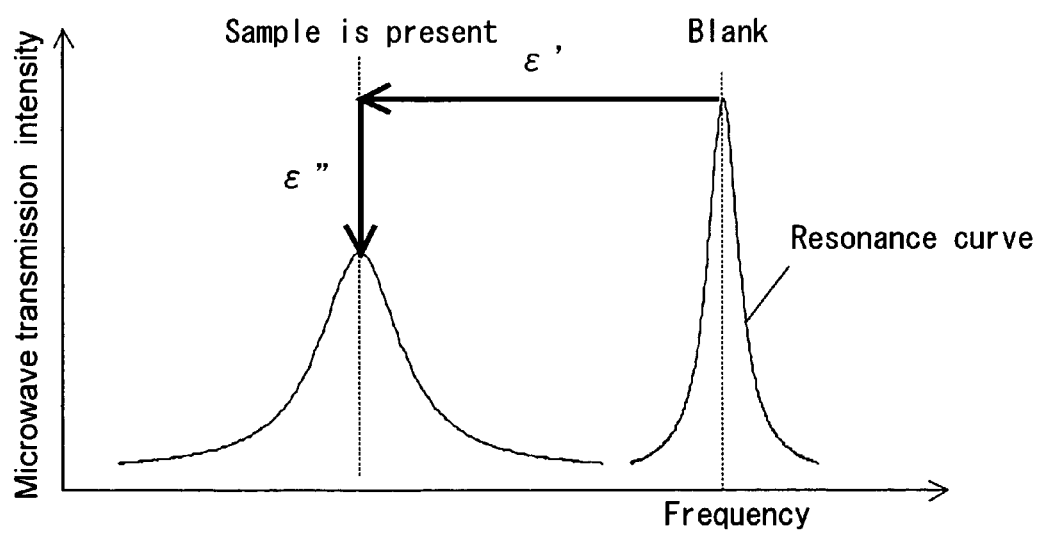
FIG. 5 shows waveforms exhibiting the change in resonance curve according to the presence or absence of the sample containing moisture.

When the resonance is generated with the microwave resonator, resonance curves shown in FIG. 5 are obtained. The right-side resonance curve is one in which the sample is absent (blank). When the sample exists inside the resonator or near the resonator, both the peak level and the Q value are decreased by the dielectric loss at the same time when the resonance frequency is shifted to the low-requency side by the dielectric constant possessed by the sample like the left-side resonance curve. The moisture content amount or the moisture content ratio is measured by taking note of the change in peak level of the resonance curve by the dielectric loss.

Figure 6:
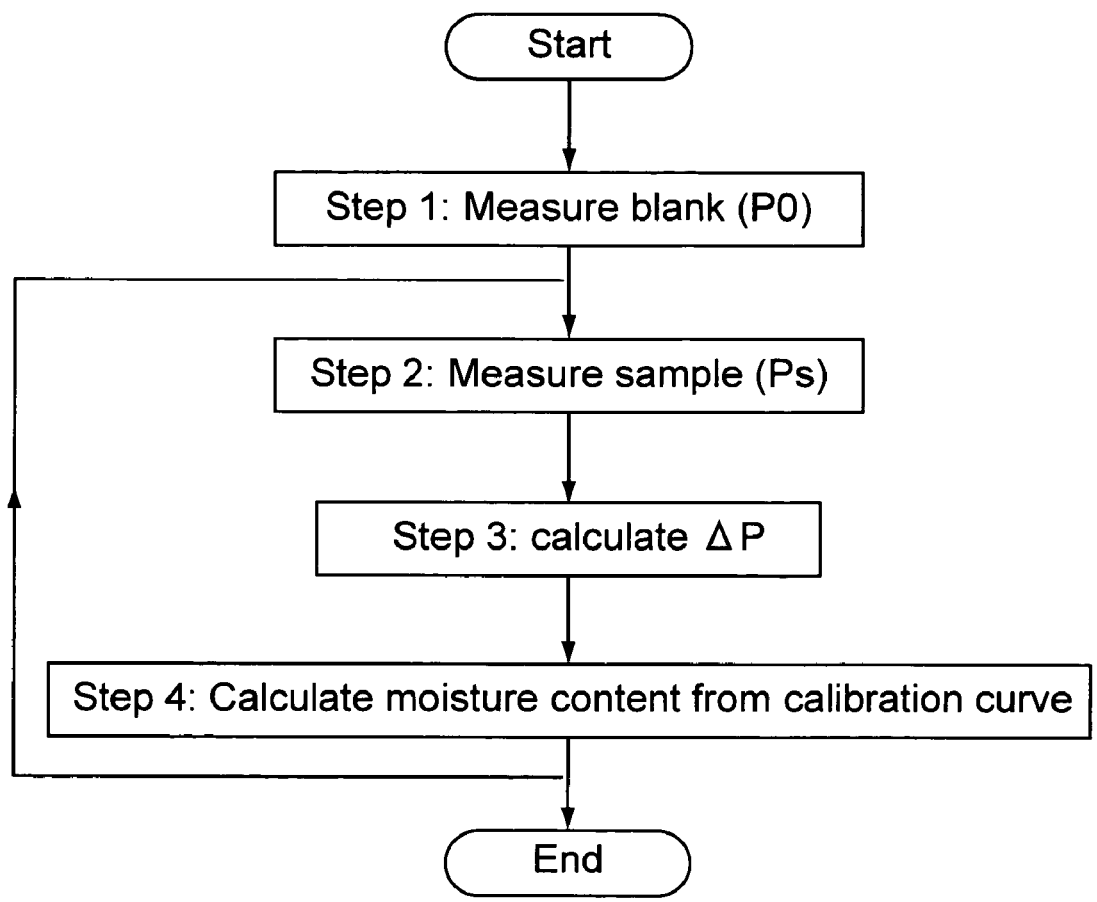
FIG. 6 is a flowchart showing a method of measuring moisture content of the sample having a constant thickness.

The measurements of the sample having a known constant thickness "t" will be described below with reference to a flowchart shown in FIG. 6. In Step 1, a resonance peak level P0 is measured in the state in which the sample does not exist (blank). In Step 2, a resonance peak level Ps of the sample is measured.

In Step 3, the difference ΔP (=P0−Ps) between both is calculated. The difference ΔP is proportional to a value $\epsilon''\cdot t$ in which dielectric loss $\epsilon''$ of the sample and the thickness t of the sample are multiplied together. Therefore, when the relationship between the moisture content and ΔP is previously determined as the calibration curve for the sample having the same thickness "t", the moisture content is obtained from the value of ΔP determined in Step 3. For example, moisture conditioning is performed on the sample in at least three conditions in which absolute humidities of the sample are different from one another, and the moisture content (weight %) and ΔP are measured in each condition to prepare the calibration curve expressing the relationship between the moisture content (weight %) and ΔP. In Step 4, ΔP determined in Step 3 is applied to the calibration curve to determine the moisture content. In a case of the online measurements, Steps 2 to 4 can be repeated at predetermined intervals.

Figure 7:
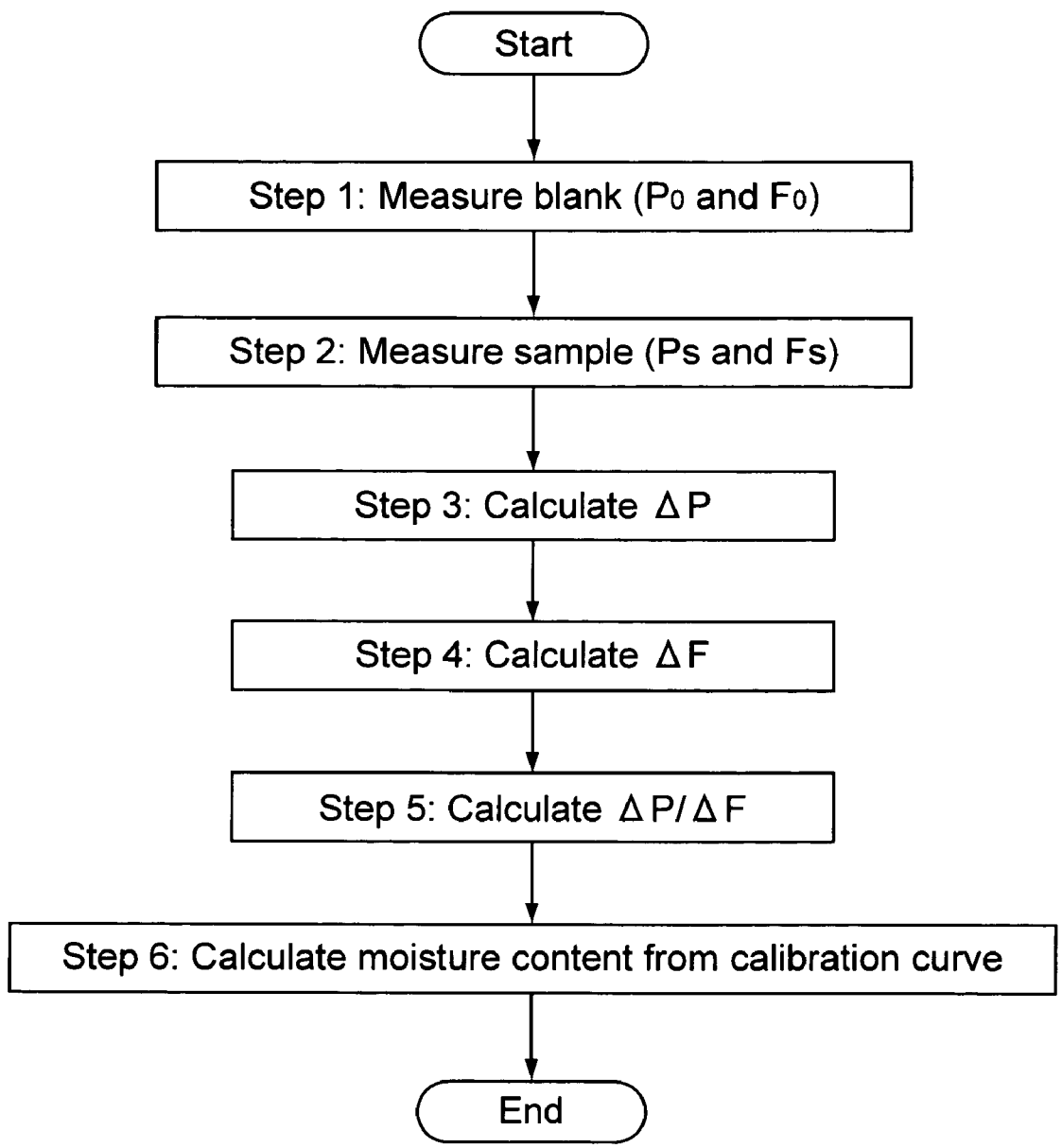
FIG. 7 is a flowchart showing a method of measuring the moisture content of the sample having a non-constant thickness.

The method of measuring the sample whose thickness is not constant will be described below with reference to a flowchart shown in FIG. 7. In Step 1, the resonance peak level P0 and a resonance frequency F0 are measured in the state in which the sample does not exist (blank). In Step 2, the resonance peak level Ps of the sample and a resonance frequency Fs are measured. In Step 3, the difference ΔP (=P0−Ps) between the blank and the sample is calculated.

In Step 4, the difference ΔF (=F0−Fs) between the blank and the sample is calculated. In the cavity resonator, the dielectric constant $\epsilon'$ is expressed by Formula (16).

$$\epsilon'-1=K1\times\Delta F/t \qquad \text{[Formula (16)]}$$

On the other hand, the difference ΔP is proportional to $\epsilon''\cdot t$ as described above, so that Formula (17) is obtained.

$$\epsilon''=K2\times\Delta P/t \qquad \text{[Formula (17)]}$$

Here, K1 and K2 are apparatus constants respectively.

When "t" is eliminated from Formulas (16) and (17), Formula (18) is obtained.

$$\epsilon''=K2/K1\cdot(\epsilon'-1)\times(\Delta P/\Delta F) \qquad \text{[Formula (18)]}$$

When the dielectric constant $\epsilon'$ is constant, Formula (18) can be expressed by Formula (19).

$$\epsilon''=K3\times(\Delta P/\Delta F) \qquad \text{[Formula (19)]}$$

Where, K3 is a constant.

That is, in a case where the film of the sample contains the trace amount of moisture, namely, in a case of constant $\epsilon'$, $\epsilon''$ is proportional to ΔP/ΔF irrespective of the thickness "t" of the sample. Therefore, ΔP/ΔF determined in Step 5 becomes a value correlated to the moisture content ratio. At this point, similarly to the case in which the thickness is constant, when the calibration curve is previously made, the moisture content ratio is determined from $\Delta P/\Delta F$ by the calibration curve (Step 6).

For a sample in which one or plural coating layers are provided over one or both surface sides while the film is used as a base material like a coating film, the method of determining the moisture content ratio in each layer will be described below.

(Measurements of $\Delta\epsilon''$ of Coating Layer)

With a sample of PET(poly ethylene telephthalate) film with a first coating layer and another sample of PET film without a coating layer, the moisture conditioning is performed at room temperature and ordinary humidity, and dielectric loss $\epsilon''_{wet}$ is determined in the state in which the moisture reaches an equilibrium state using a molecular orientation meter. Dielectric loss $\epsilon''_{first\ coating\ layer\ wet}$ of the first coating layer only is determined at room temperature and humidity from the dielectric losses of the two samples. Then, dielectric loss $\epsilon''_{dry}$ is determined in the state in which the moisture is sufficiently removed using the molecular orientation meter, and dielectric loss $\epsilon''_{first\ coating\ layer\ dry}$ is similarly determined in the state in which the moisture is removed. The difference $\Delta\epsilon''$ between both corresponds to the moisture content amount (namely, moisture content ratio) per unit area of the first coating layer.

Dielectric loss $\epsilon''_{second\ coating\ layer}$, dielectric loss $\epsilon''_{third\ coating\ layer}$, ... of a second coating layer, a third coating layer, ... are similarly determined. These values are an intrinsic physical property value at the measuring condition of room temperature and humidity.

(Measurements of Thickness)

A thickness $t_{base}$ of the base film, thicknesses $t_{first\ coating\ layer}$, $t_{second\ coating\ layer}$, $t_{third\ coating\ layer}$, ..., and a total thickness $t_{total}$ are determined from a thickness meter, a coating amount, and the like.

(Calculation of Moisture Content of Each Coating Layer)

Figure 8:
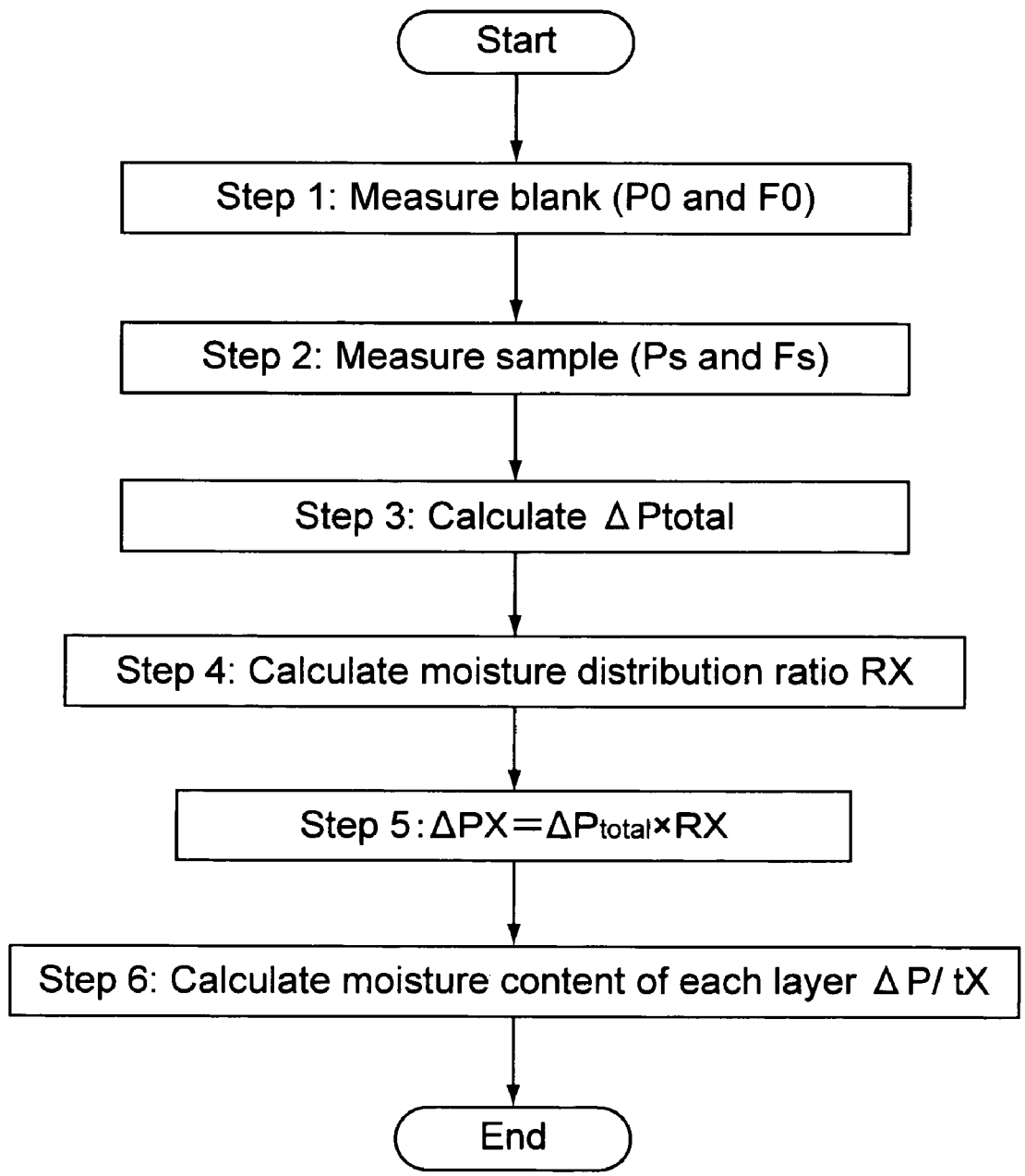
FIG. 8 is a flowchart showing a method of measuring the moisture content of a coating layer of the sample.

The measurement procedure will be described with reference to a flowchart of FIG. 8.

In Step 1, the resonance peak level P0 is measured in the state in which the sample does not exist (blank). The resonance peak level Ps of the samples including coating films in which one or plural coating layers are applied is measured in Step 2.

In Step 3, the difference $\Delta P_{total}$ (=P0−Ps) between both is calculated. In this case, a distribution ratio of the moisture amount contained in the base film and each coating layer to the total moisture amount contained in the whole of the coating film will be discussed. It is assumed that "W" is the total moisture amount. When the moisture reaches the equilibrium state among the coating layers, the total moisture amount "W" can be expressed by Formula (20) using $\Delta\epsilon''$ of each layer and the thickness "t".

$$W = \Delta\epsilon''_{base} \cdot t_{base} + \epsilon''_{first\ coating\ layer} \cdot t_{first\ coating\ layer} + \Delta\epsilon''_{second\ coating\ layer} \cdot t_{second\ coating\ layer} + \Delta\epsilon''_{third\ coating\ layer} \cdot t_{third\ coating\ layer} + \cdots \quad \text{[Formula (20)]}$$

Therefore, a distribution ration $R_x$ to each layer is expressed by Formula (21).

$$R_x = \Delta\epsilon''_x t_x / W \quad \text{[Formula (21)]}$$

Here, X indicates either the base film or each coating layer.

In Step 4, the moisture distribution ratio of each layer is determined from $\Delta\epsilon''$ of each layer and the thickness "t" in the above procedure. Because the $\Delta P_{total}$ is proportional to the total moisture content amount of the coating film, the moisture content amount of each layer becomes a value proportional to $\Delta P_x$ determined by Formula (22) (Step 5).

$$\Delta P_x = \Delta P_{total} \times R_x \quad \text{[Formula (22)]}$$

Therefore, $\Delta P_x t_x$ becomes a value correlated with the moisture content ratio of each layer (Step 6). In a case of the online measurements, Steps 2 to 6 can be repeated at fixed intervals.

The grammage measurements of the invention can also be realized with an orientation meter. In the orientation meter, the dielectric resonator is used, and fiber orientation of the paper or the molecular orientation of a molecular sheet such as the film is measured online from the change in resonance frequency. In this case, an average value of dielectric resonator outputs in orientation directions used in the orientation measurements is used for the grammage measurements.

Japanese Patent Laid-Open No. H10-325811 discloses an orientation meter in which the dielectric resonator is utilized. In the orientation meter disclosed in Japanese Patent Laid-Open No. H10-325811, the plural dielectric resonators are arranged, and the fiber orientation of the paper or the molecular orientation of the film is measured online from the resonance frequency shift amount in each dielectric resonator.

Figure 9:
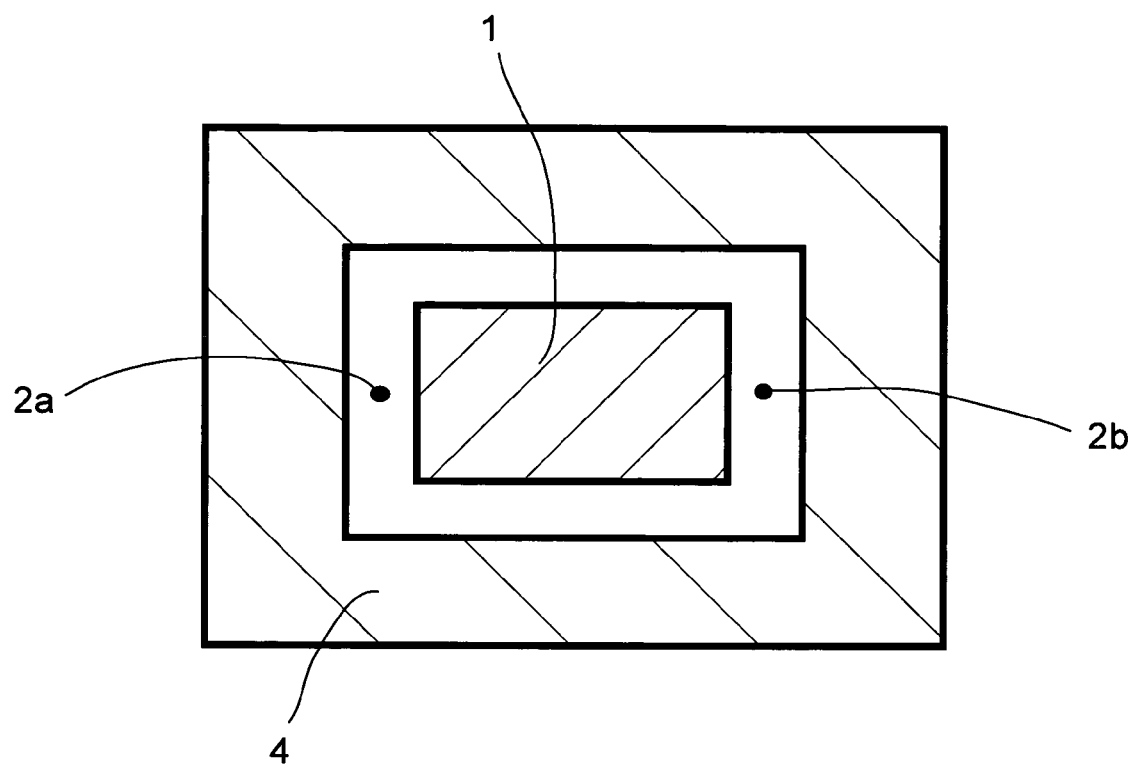
FIG. 9 is a plan view showing a rectangular dielectric resonator used in measuring sample orientation.
Figure 10:
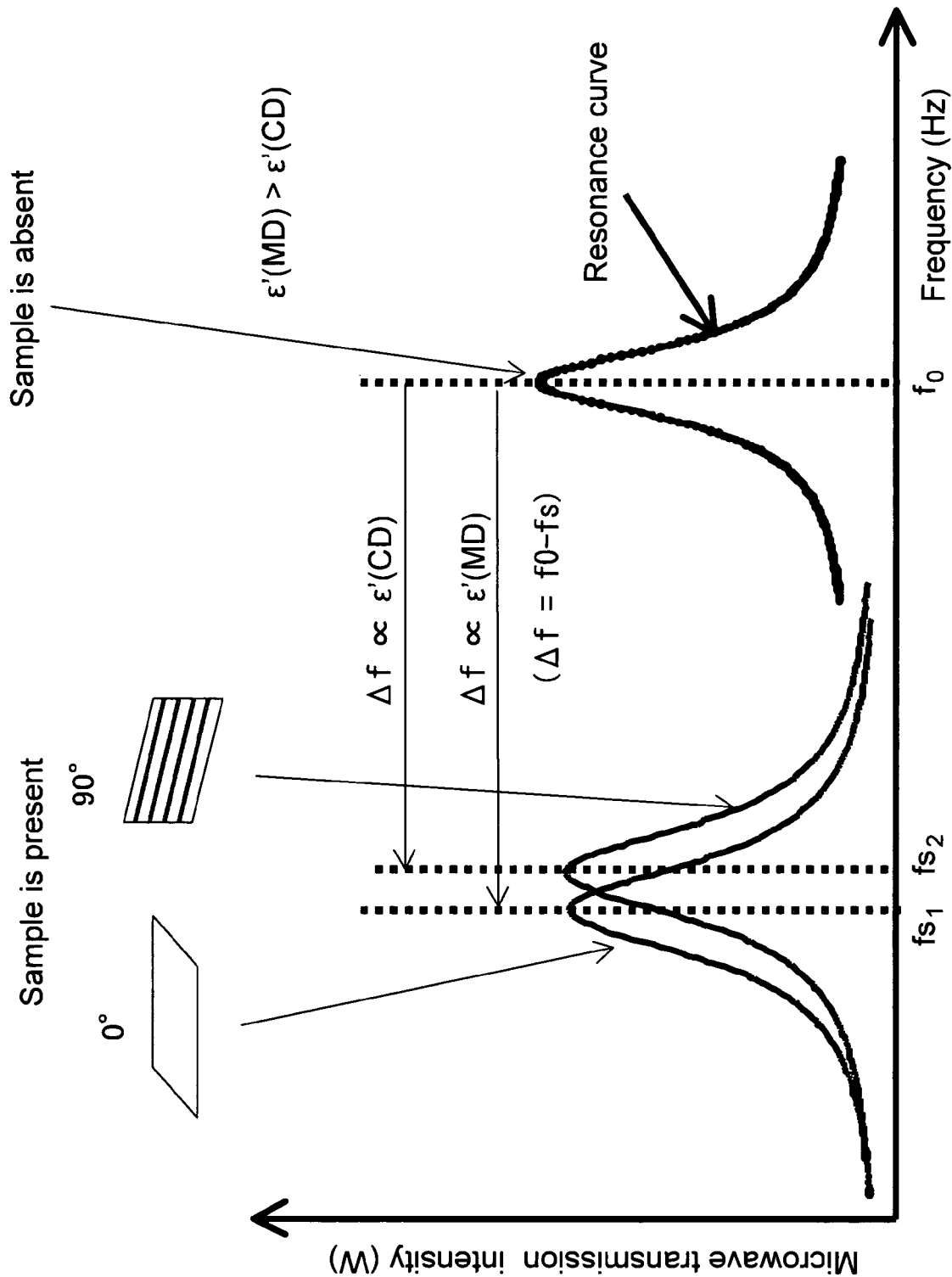
FIG. 10 shows waveforms exhibiting a resonance frequency shift according to the presence or absence of the sample in the orientation measurements.
Figure 11:
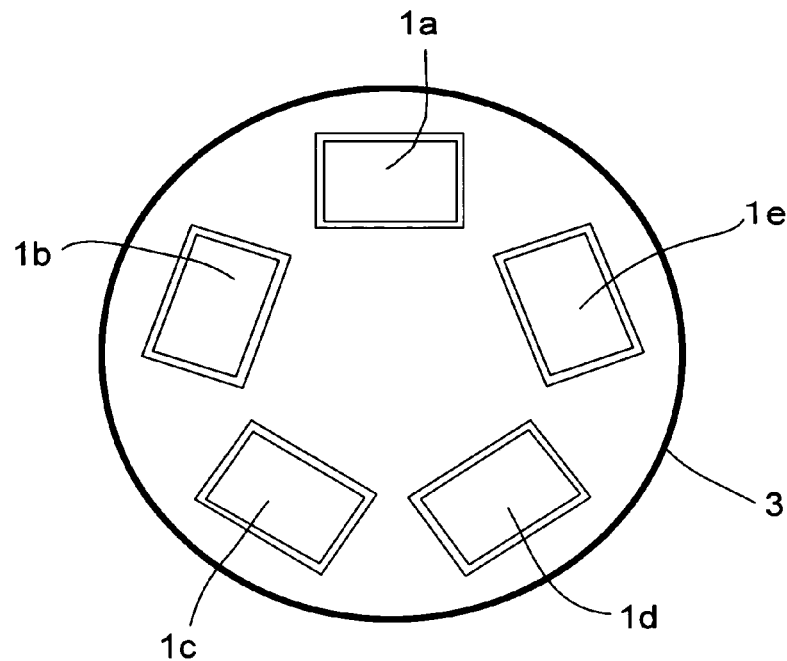
FIG. 11 is a plan view showing an orientation measuring unit in which five dielectric resonators are arranged.
Figure 12:
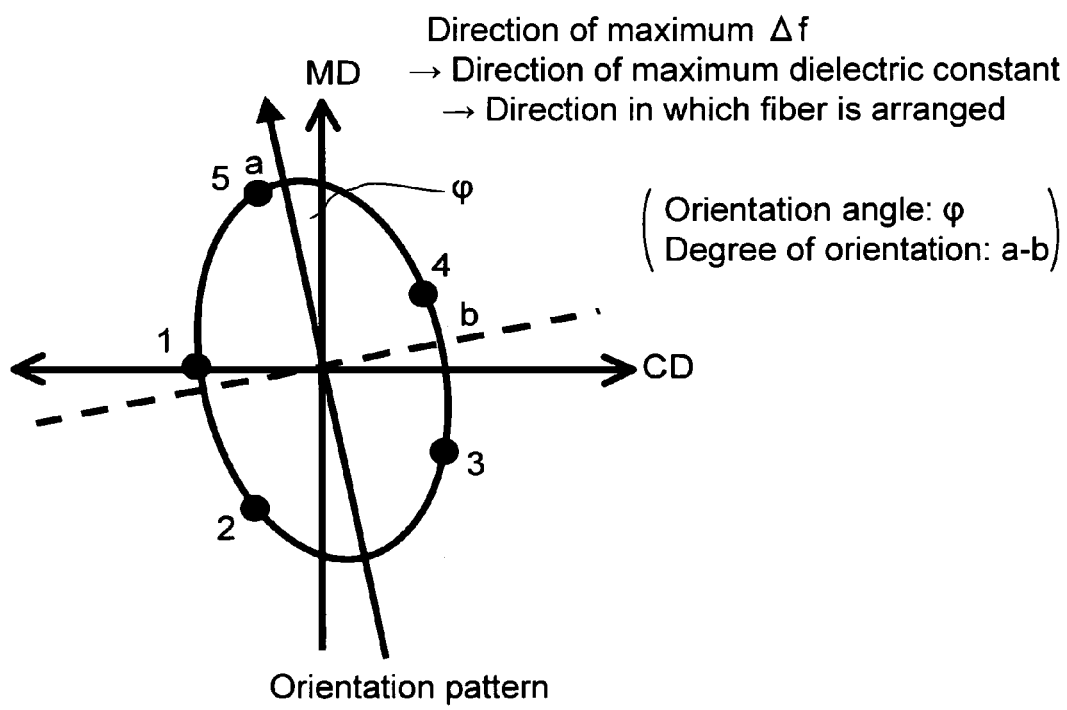
FIG. 12 shows an example of an orientation pattern obtained from the five dielectric resonators of FIG. 11.

For example, the dielectric resonator shown in FIG. 9 is used in this method. FIG. 9 is a plan view showing a structure of the dielectric resonator. The rectangular dielectric resonator 1 is excited by one antenna 2a, and the other antenna 2b outputs the resonance frequency. The rectangular dielectric resonator 1 and the antennas 2a and 2b are accommodated in the shielding container 4. When the sample is placed near the dielectric resonator 1, as shown in FIG. 10, the resonance frequency is shifted from the blank state in which the sample does not exist to the low-frequency side. FIG. 10 shows the resonance frequency shift according to the change in dielectric constant caused by the presence or absence of the sample in the dielectric resonator. In FIG. 10, the sign MD designates a paper flow direction (machine direction) of the paper machine and the sign CD designates a direction (cross direction) at right angles to the paper flow direction of the paper machine in a case where the sample is a paper. Because the shift amount expressed by $\Delta f = f_0 - f_1(f_2)$ is proportional to a product of the dielectric constant and thickness of the sample, when each of five rectangular dielectric resonators 1a to 1e is arranged at an angle of, for example, 72° from the adjacent dielectric resonators as shown in FIG. 11 to plot each shift amount on a polar coordinate, an orientation pattern corresponding to the dielectric constant anisotropy is obtained as shown in FIG. 12. FIG. 11 is a plan view showing an orientation measuring unit 3 in which the five dielectric resonators are arranged. FIG. 12 shows an example of the orientation pattern obtained from the five dielectric resonators shown in FIG. 11. The orientation direction of the fiber or molecular chain is determined from a major axis of the orientation pattern shown in FIG. 12, and a degree of orientation is found from a difference or a ratio between the major axis and the minor axis.

Conventionally, when the fiber orientation of the paper running is actually measured online based on the above measuring principle, various problems occurred. One of the problems is that the resonance frequency shift amount cannot appropriately be measured. Therefore, the original orientation pattern is not obtained. The inventors performed various kinds of measurements for the paper orientation by the contact method. The inventors presumed it is attributed to the fact that the contact state is fluctuated due to a flutter of the running paper to vary a gap between the paper and the measuring surface of the dielectric resonator and thereby the measured resonance frequency is fluctuated. However, as a result of the actual online measurements, it was found that the resonance frequency is not appropriately measured.

Figure 13:
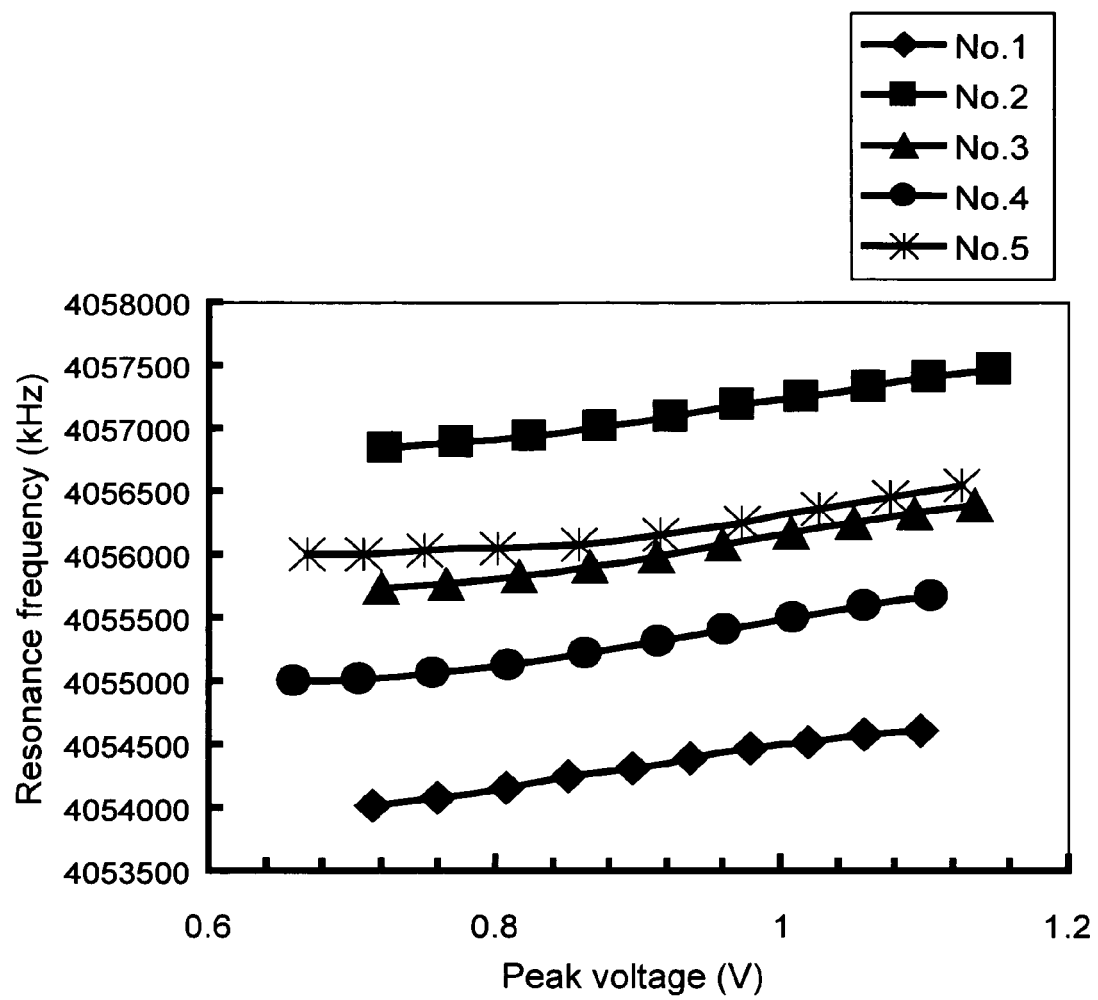
FIG. 13 is a graph showing a relationship between a resonance peak level (displayed in voltage) and a resonance frequency at that time for each dielectric resonator.

The consideration of the cause of the fluctuation is as follows: Originally the resonance frequency of the dielectric resonator is independent of the resonance peak level. That is, the resonance frequency should be maintained constant even if microwave power inputted to the dielectric resonator is changed to vary the resonance peak level. However, in actuality, it was found that the resonance frequency is changed when the resonance peak level is varied. For example, as shown in FIG. 13, the resonance frequency tends to be increased as the resonance peak level is increased. FIG. 13 shows an example of the relationship between the resonance peak levels and the resonance frequencies for the dielectric resonators No. 1 to No. 5 of the orientation measuring unit 3 shown in FIG. 11.

Figure 14:
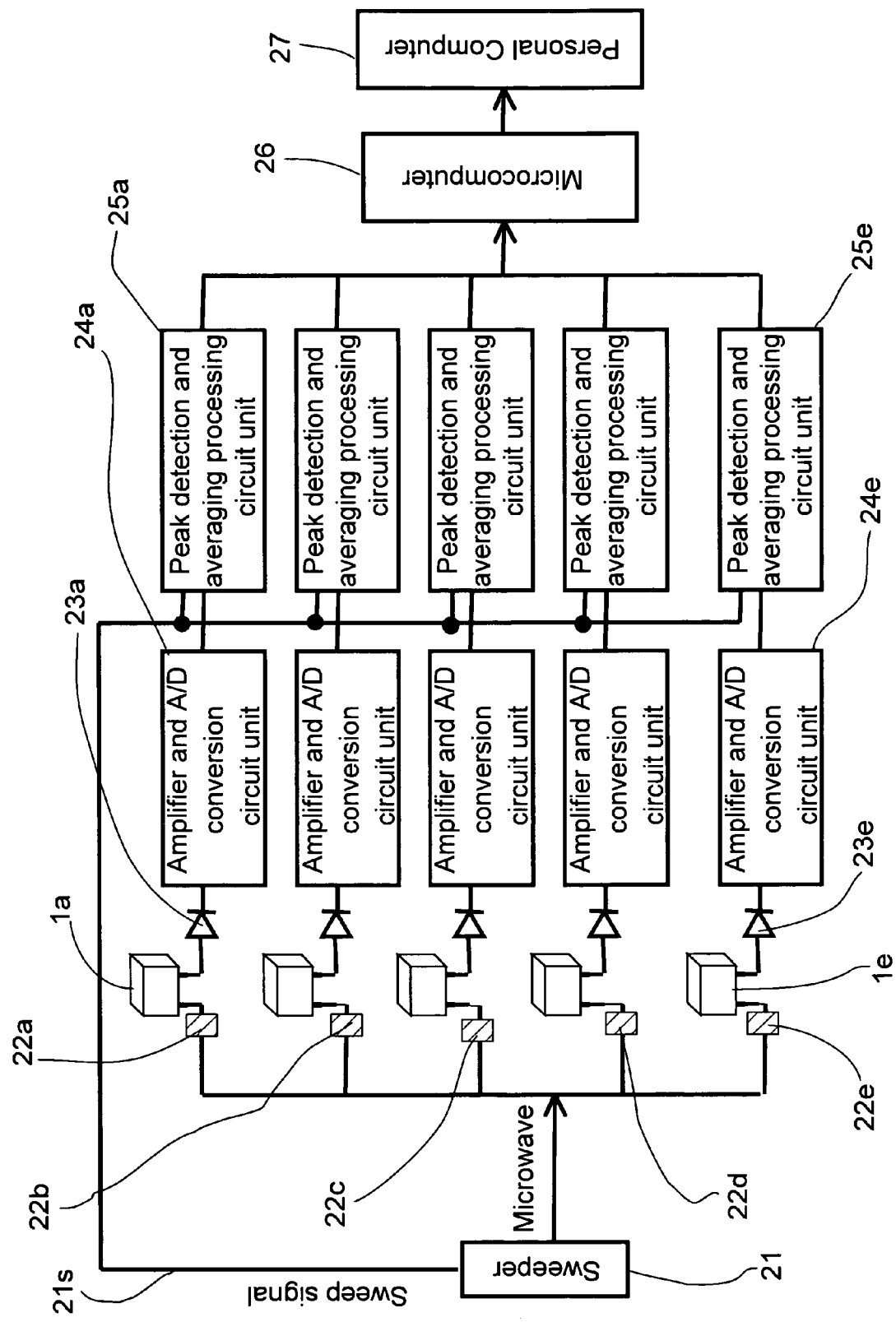
FIG. 14 is a block diagram showing a circuit which processes signals from the five dielectric resonators.
Figure 15:
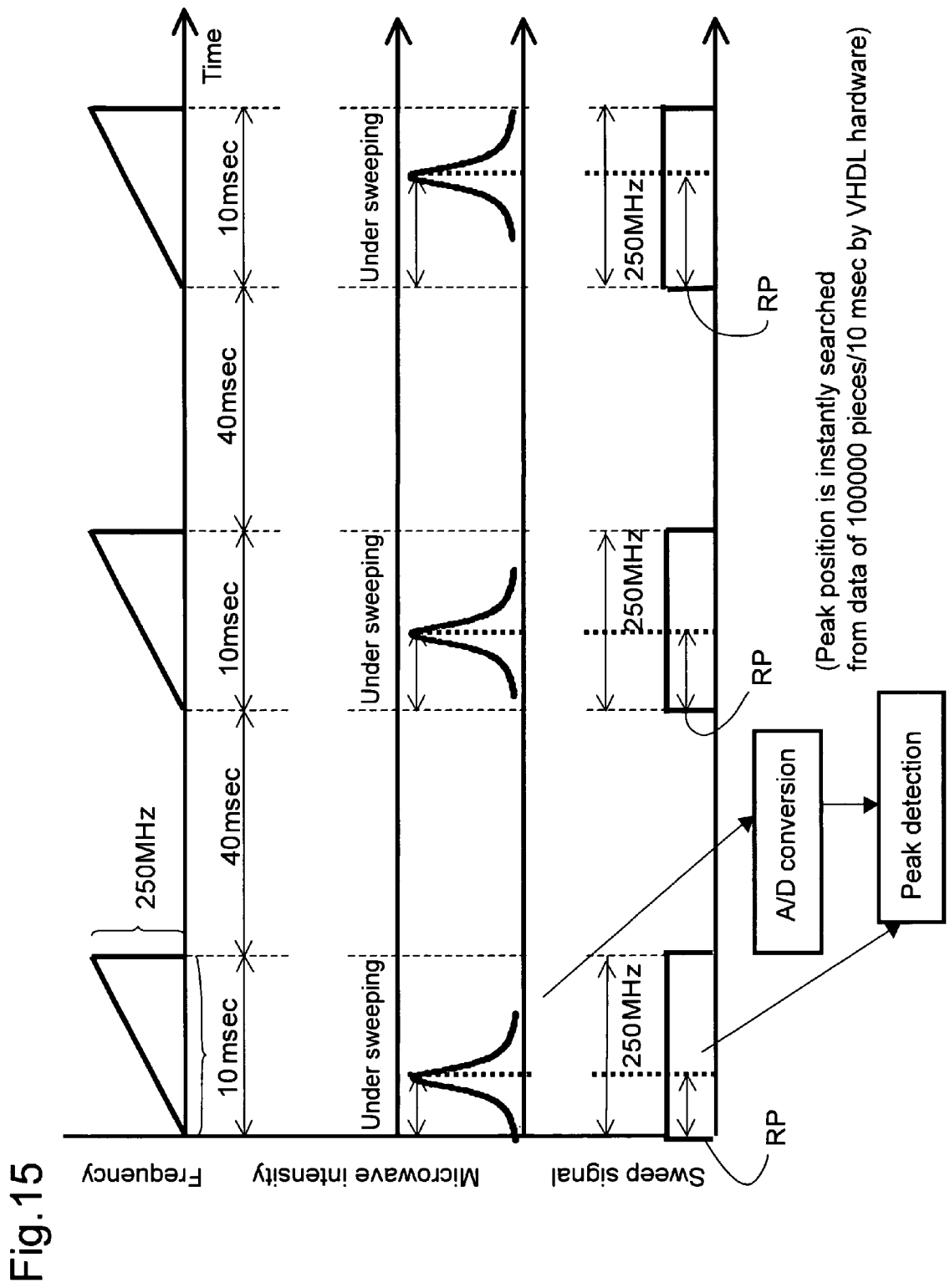
FIG. 15 is a timing chart showing the signal processing in the block diagram of FIG. 14.

The inventors found that the change in resonance frequency is caused by an amplifier circuit In order to measure the resonance frequency at high speed close to real time, the resonance frequency is measured by a timing chart shown in FIG. 15 using a signal processing system shown in FIG. 14. FIG. 14 is a block diagram showing the circuit which processes signals from the five dielectric resonators. FIG. 15 is the timing chart showing the signal processing in the block diagram shown in FIG. 14. The signals outputted from a microwave sweep oscillator 21 which is of microwave oscillation means are distributed to dielectric resonators 1a to 1e through isolators 22a to 22e. In FIG. 14, the microwave sweep oscillator is indicated as sweeper. The output from the dielectric resonator is converted into voltage by detection diodes 23a to 23e, and the voltage is inputted to peak detection and averaging processing circuit units 25a to 25e through amplifier and A/D conversion circuit units 24a to 24e. As shown in FIG. 15, frequency is swept by the microwave sweep oscillator, a start pulse portion is detected from a sweep signal 21s to measure a time until the resonance level reaches the peak, and the resonance frequency is determined from the time by proportional calculation. For example, when the frequency is continuously increased by 250 MHz sweep around 4 GHz, the resonance curve is obtained from microwave transmission intensity. The peak frequency of the resonance curve becomes the resonance frequency to be determined. Because sweep start timing can be detected by the start pulse portion which is of a leading edge of the sweep signal, the time to reach the peak level is measured from the sweep start timing, and the resonance frequency is measured by calculating the sweep speed of 250 MHz at the duration of 10 msec. The resonance frequency measurements are repeated at intervals of 50 msec, and 20 resonance frequency measurement values are averaged to obtain the resonance frequency. Thus, one sweep time is as extremely short as 10 msec, and the signal is amplified at high speed to perform digital processing.

Figure 16:
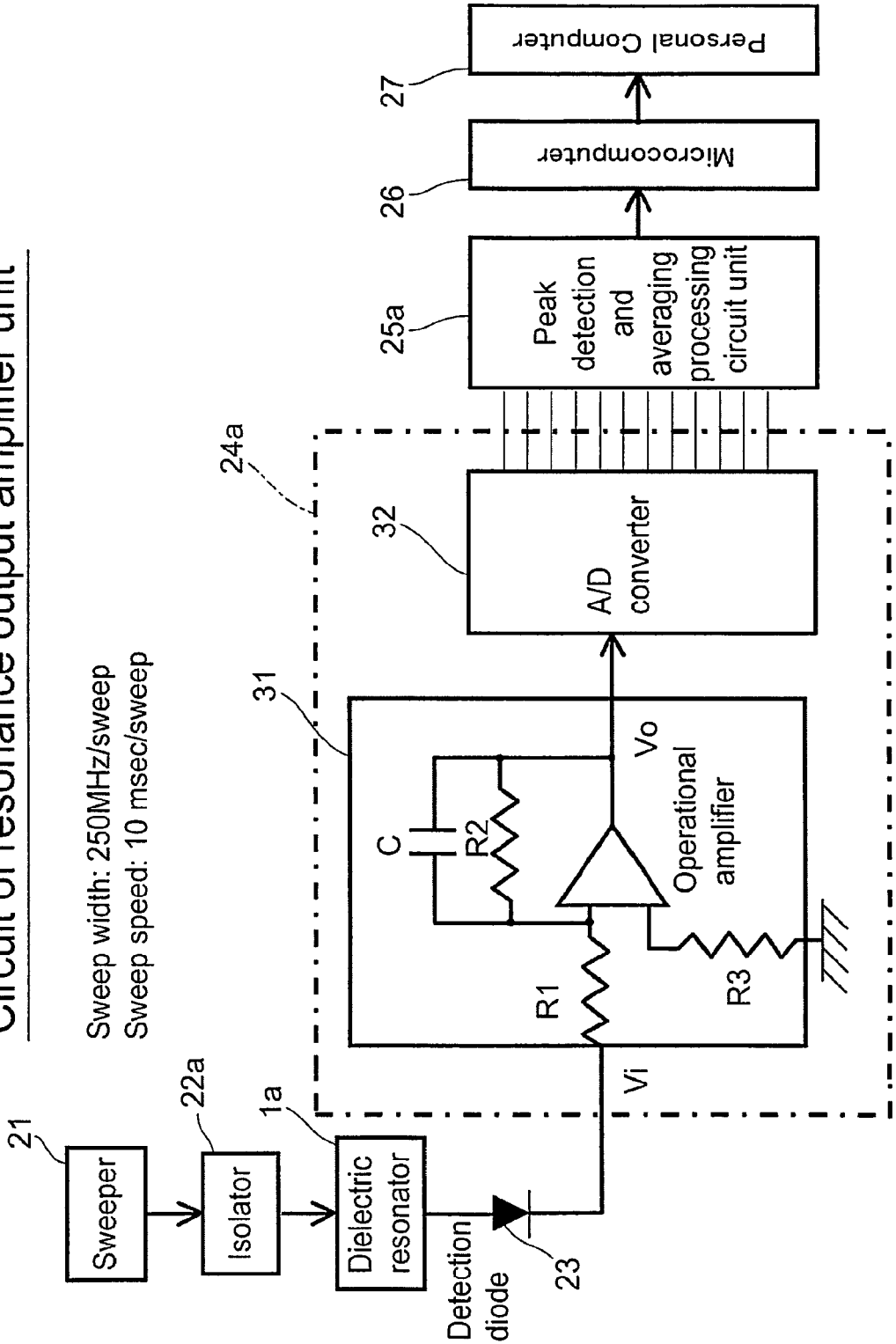
FIG. 16 is a detailed block diagram showing the signal processing circuit for one of the dielectric resonators in the circuit of FIG. 14.

FIG. 16 shows a detailed circuit diagram for one of the dielectric resonators in the circuit shown in FIG. 14, namely, for one of the dielectric resonator detection system circuits. For example, the amplifier and A/D conversion circuit unit 24a includes an amplifier circuit 31 and an A/D converter unit LSI 32. The digital output from the amplifier and A/D conversion circuit unit 24a is inputted to the peak detection and averaging processing circuit unit 25a. For example, the peak detection and averaging processing circuit unit includes a peak detection LSI and an averaging processing LSI. Correctly the peak detection LSI has a resonance peak level detection circuit which detects the resonance peak and the averaging processing LSI performs the averaging processing of the resonance peak frequency obtained in each sweep.

A microcomputer unit 26 is connected to a post-stage of the peak detection and averaging processing circuit unit 25a. The microcomputer unit 26 collectively transmits the signal from each dielectric resonator detection system to a post-stage personal computer 27, and the microcomputer unit 26 has a function of controlling and operating the amplifier and A/D conversion circuit units 24a to 24e and the peak detection and averaging processing circuit units 25a to 25e in each dielectric resonator system. The personal computer 27 is connected to the microcomputer unit 26. The personal computer 27 computes the output from the microcomputer unit 26 to measure the orientation or the amount of orientation, and the personal computer 27 displays and stores the orientation or the amount of orientation as data.

Here, because the post-amplification output contains a ripple caused by a noise, an RC circuit including a capacitor C1 and a resistor R2 is inserted into a feedback line in the amplifier circuit 31 in the amplifier and A/D conversion circuit unit 24a of FIG. 16, which allows the ripple voltage to be absorbed and reduced to obtain direct-current voltage having little fluctuation. Therefore, it is necessary that the amplifier circuit have the capacitor C1.

Figure 17:
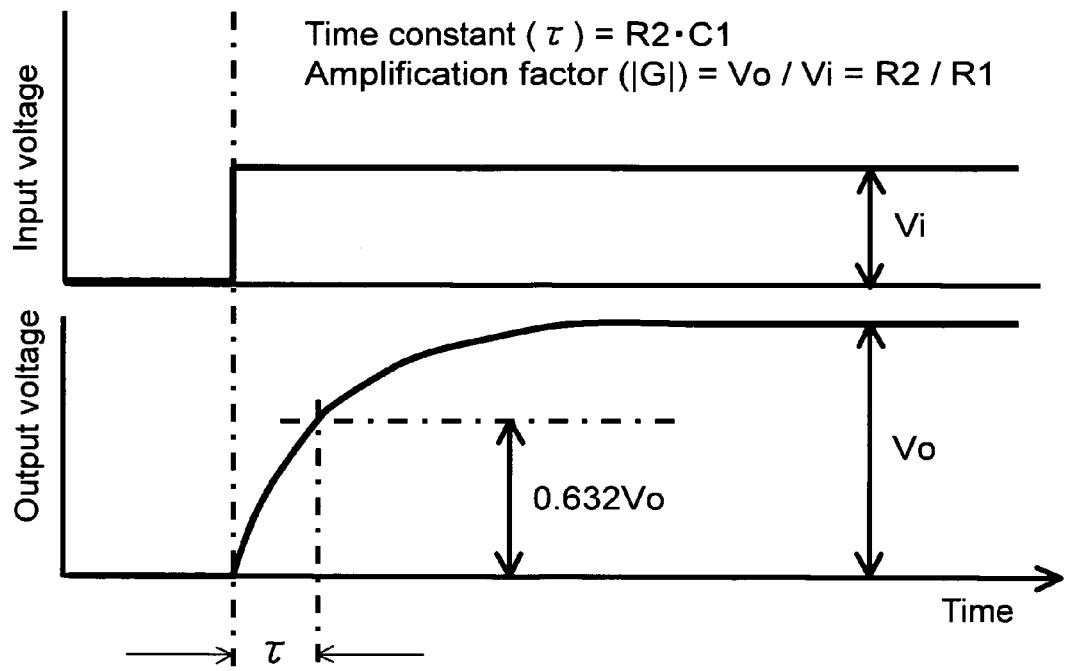
FIG. 17 is a waveform chart showing a step input waveform inputted to an amplifier circuit and a waveform outputted from the amplifier circuit.

The capacitor C1 and the resistor R2 become a so-called time delay factor, and thereby delay (time constant) shown in FIG. 17 is generated in the amplifier circuit. FIG. 17 is a waveform chart showing a stepwise input waveform inputted to the amplifier circuit and a waveform outputted from the amplifier circuit. Even if the ideal stepwise pulse Ps having an extremely short rise time is inputted, the output waveform of the amplifier does not become the ideal stepwise shape, but the response waveform having the gentle rise time is obtained. The time to reach 63.2% of the final output voltage is generally called time constant $\tau$, and the time constant $\tau$ is expressed by the capacitance C1 of the capacitor and the resistance value R2. That is, time constant $(\tau)$=R2·C1, and amplification factor $(|G|)$=Vo/Vi=R2/R1. Where Vo is output voltage, and Vi is input voltage.

Figure 18:
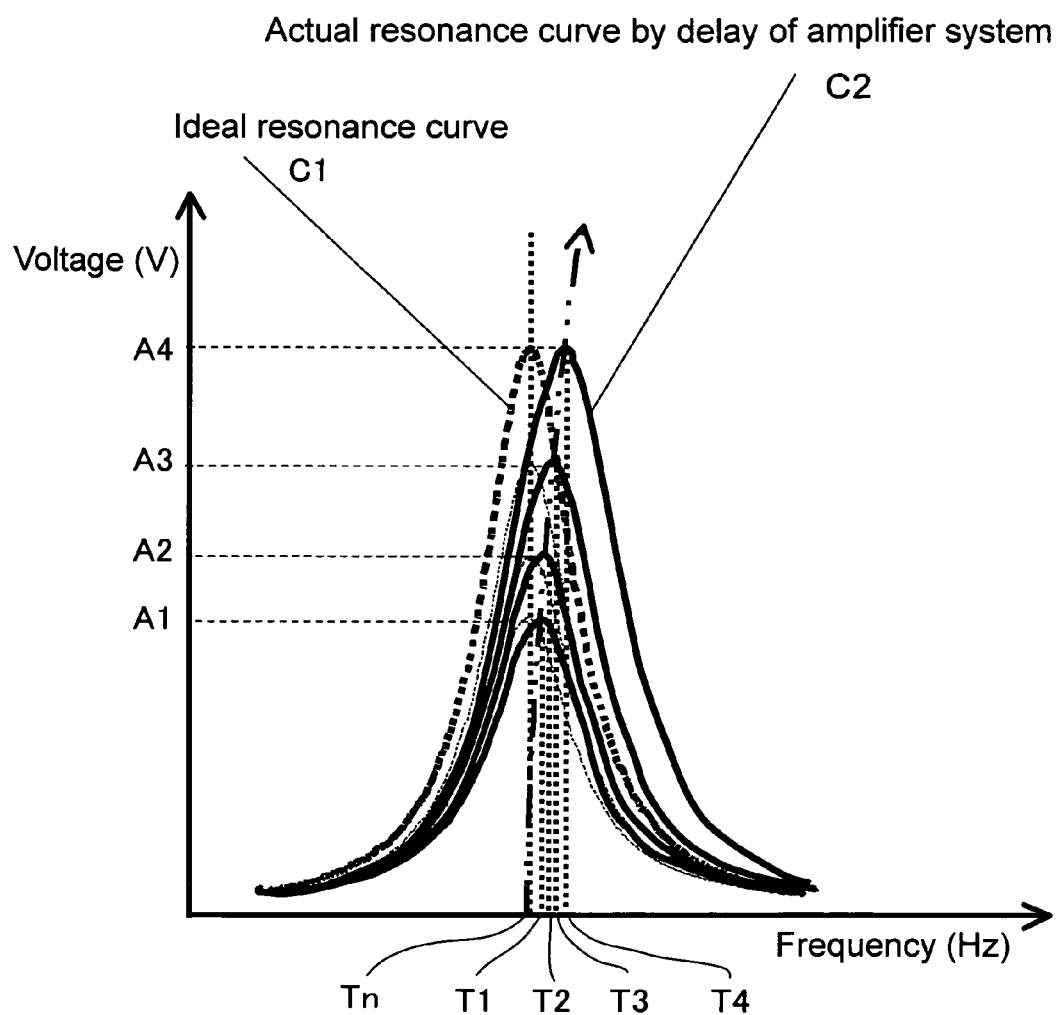
FIG. 18 shows waveforms showing a relationship between the resonance curve and the resonance peak level voltage.

When the resonator output in a case where the sweep is performed at high speed with sweep time of 10 msec is inputted to the circuit in which the above amplifier circuit is used, as shown in FIG. 18, the post-amplification resonance curve waveform is changed in the resonance peak level voltage. FIG. 18 shows the change in resonance curve according to the rise of the resonance peak level voltage in the resonance curve. The resonance curve should ideally be symmetrical even if the resonance peak level voltage rises. However, in actuality, the resonance curve is shifted from the symmetrical shape and bent to the high frequency side. As can be seen from FIG. 18, the resonance peak frequency is shifted to the higher resonance peak frequency side as the resonance peak level voltage is increased. That is, even in the same resonance system including the same circuit, a phenomenon that the resonance peak frequency which should not be changed is changed, is generated only by changing the resonance peak level voltage, which leads to the fact that the real resonance frequency cannot be measured. In FIG. 18, the ideal resonance curve C1 having the highest peak level becomes the actual resonance curve C2 generated by delay of the amplifier system.

The resonance peak level voltage shift has no influence on an orientation measuring apparatus according to the preferred embodiment of the invention.

The orientation measuring apparatus includes a plurality of dielectric resonator detection systems. Each of the dielectric resonator detection systems includes a dielectric resonator, an amplifier circuit, a resonance peak level detection circuit, and variable electric signal attenuation and amplification means.

The dielectric resonator is connected to the microwave oscillation means. The amplifier circuit is connected to the dielectric resonator to amplify the output of the dielectric resonator, and the amplifier circuit includes a time delay element. The resonance peak level detection circuit is connected to the amplifier circuit to detect the resonance peak level from the output of the amplifier circuit The variable electric signal attenuation and amplification means is inserted between the microwave oscillation means and the resonance peak level detection circuit. The orientation measuring apparatus includes control means. The control means compares the output from the resonance peak level detection circuit of each dielectric resonator detection system to a predetermined resonance peak level to generate a signal for changing an attenuation degree or an amplification degree to the variable electric signal attenuation and amplification means so that the output is brought close to the predetermined peak level.

The computer as the control means compares the output from the resonance peak level detection circuit to the predetermined resonance peak level and transmits the signal for changing the attenuation degree or the amplification degree to control the programmable attenuator as the variable electric signal attenuation and amplification means so as to bring the output close to the predetermined peak level. Therefore, because the resonance peak level is always kept constant, the orientation can be measured while the resonance peak frequency shift from the real value caused by the resonance peak level shift hardly has an influence on the orientation measurements.

It is preferable that the dielectric resonator detection system have an analog and digital conversion circuit unit (A/D conversion circuit) and the predetermined peak level voltage be set within an input range of the analog and digital conversion circuit unit. This is because accuracy is improved by setting the input range of the analog and digital conversion circuit unit as large as possible. When the predetermined resonance peak level voltage is slightly decreased from the maximum value of the input range, a margin is secured in overshoot.

It is preferable that the variable electric signal attenuation and amplification means be a programmable attenuator and be connected between the dielectric resonator and the microwave oscillator from the viewpoint of configuration.

The variable electric signal attenuation and amplification means may also be used as the amplifier circuit In this case, it is preferable that an amplification factor of the amplifier circuit be variable in an analog or digital manner.

In an orientation measuring method in the orientation measuring apparatus, the outputs from the plural dielectric resonators connected to the microwave oscillation means are amplified, each resonance peak level is detected from each amplified output, the resonance peak level of each dielectric resonator is compared to the predetermined resonance peak level, and the output from the microwave oscillation means to the dielectric resonator or the output from the dielectric resonator is attenuated or amplified so that the resonance peak level of each dielectric resonator is brought close to the predetermined resonance peak level.

In the method and apparatus for measuring the orientation, an error is further decreased in the resonance frequency measurements when the resonance frequency is determined from the resonance peak of the dielectric resonator. The orientation can be measured more correctly in measuring the degree of orientation from the difference in resonance frequency between the absence and presence of the sample.

In FIG. 18, it is thought that resonance peak frequencies T1, T2, T3, and T4 corresponding to the fluctuations of resonance peak levels A1, A2, A3, and A4 are corrected to the original positions indicated by a normal position Tn. However, it is actually difficult to realize the correction of the resonance peak frequencies T1, T2, T3, and T4, because it is necessary to perform a substantial amount of waveform simulation.

For the purpose of convenience, the inventors thought that, when the correction is performed so that the resonance peak frequencies become a certain resonance peak level, e.g, the resonance peak level indicated by A3 in FIG. 18, the error caused by the difference in resonance peak level in each piece of data obtained by each dielectric resonator is considerably suppressed, although the resonance frequencies have the shift amounts according to the resonance peak level. Because the finally determined orientation intensity is determined based on the difference in resonance frequency between the absence and presence of the sample, even if the resonance frequencies have the shift amounts, the shift amount tends to be removed in the calculating the difference. Therefore, it is presumed that the actual shift amount is further decreased.

Figure 19:
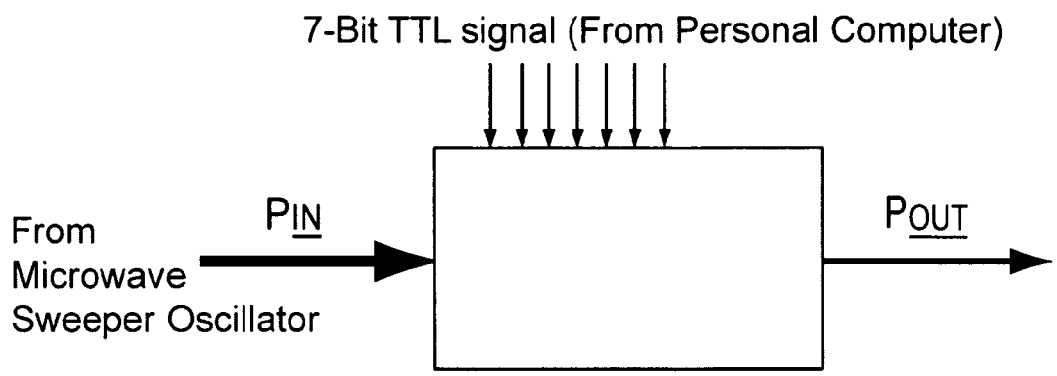
FIG. 19 is a block diagram showing action of a grammage attenuator.

As described above, when the five dielectric resonators are used, five different resonance peak levels are usually obtained. A programmable attenuator is introduced to make the five resonance peak levels uniform. The programmable attenuator obtains an arbitrary attenuation level from the electric signal so that the programmable attenuator can be called "variable electric signal attenuation means". For example, as shown in FIG. 19, in a case of the 7-bit model programmable attenuator, an arbitrary attenuation level ranging from minimum resolution of 0.125 dB to maximum resolution of 15.875 dB is obtained stepwise by combination of the electric signals (TTL level) applied to the bits. FIG. 19 shows action of the programmable attenuator. A table in FIG. 19 shows the attenuation level of the programmable attenuator corresponding to the inputted 7-bit signal. The attenuation level of microwave input Pin can be controlled and outputted as Pout to the attenuator prior to the dielectric resonator by the combination of the 7-bit signals. The attenuation level is expressed by attenuation level (dB)=−$\text{Log}_{10}$(Pout/Pin).

In measurements of this kind, generally, an attenuator is usually used so that signal shape change is minimal and a simple circuit configuration is maintained. However, when the advantages of the attenuator are neglected, the amplifier can also be used to make the resonance peak level uniform. Accordingly, the variable electric signal attenuation and amplification means can be used in principle.

It is found that the five resonance peaks in the five dielectric resonators are slightly different from one another. This is attributed to individual difference of the dielectric resonator and the like.

Figure 20:
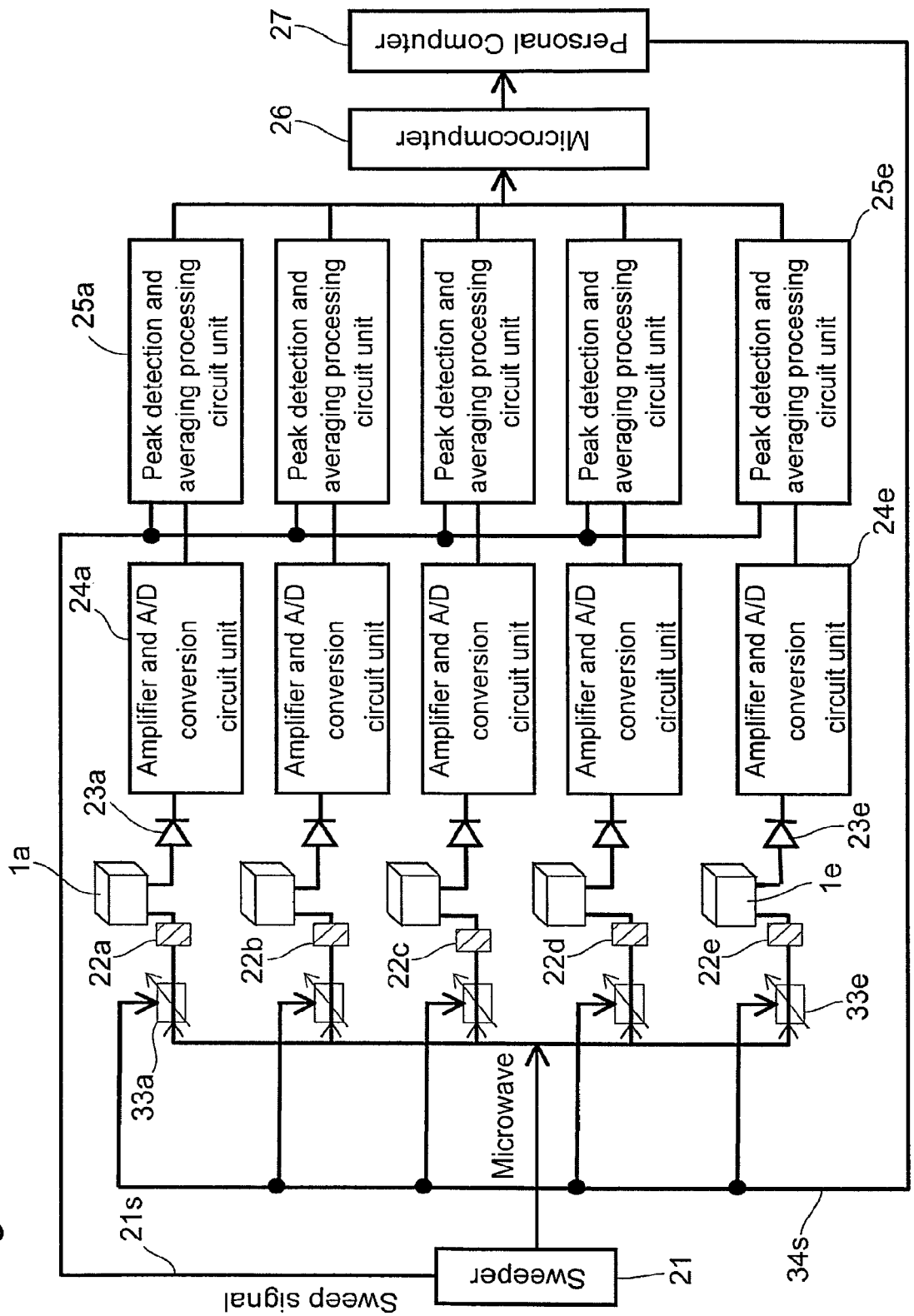
FIG. 20 is a block diagram showing a state in which the programmable attenuator is incorporated into the signal processing circuit of FIG. 14.

As shown in the block diagram of FIG. 20, the programmable attenuator is inserted, and feedback control is performed by a control loop in which the personal computer is utilized. FIG. 20 is a block diagram showing the dielectric resonator circuit of the orientation meter in the state in which the programmable attenuator is incorporated into the circuit of FIG. 14 which processes the signal from the dielectric resonator. In FIG. 20, the same component is designated by the same numeral as FIG. 14. However, the personal computer 27 shown in FIG. 20 differs from the personal computer 27 shown in FIG. 14 in that a function of controlling the programmable attenuator is added by software. In a case where the five dielectric resonators are used as shown in FIG. 14, as shown in FIG. 20, programmable attenuators 33a to 33e are inserted into the dielectric resonators respectively.

The microwaves outputted from the microwave sweep oscillator, abbreviated to sweeper in FIG. 20, is distributed and inputted to the five programmable attenuators 33a to 33e, and the microwaves are attenuated by the amount determined by the electric signal 34s. The electric signal 34s is transmitted from the personal computer 27 to each programmable attenuator. The attenuated microwaves are inputted to the five dielectric resonators 1a to 1e through the isolators 22a to 22e respectively. The resonance level is detected by the antenna located at the opposite side, and the transmission intensity is converted into voltage by each of the detection diodes 23a to 23e. Then, the voltage is transmitted to the peak detection and averaging processing circuit units 25a to 25e through the amplifier and A/D conversion circuit units 24a to 24e. The resonance frequency is measured by the peak detection LSI. In FIG. 20, the numeral of the component in each dielectric resonator detection system is appropriately neglected. Because analog ramp sweep is performed in the frequency, the rise pulse RP (see FIG. 15) of the sweep pulse outputted from the microwave sweep oscillator is detected to measure the time interval from when the rise pulse RP is detected until when the detection voltage reaches the peak. The sweep speed (frequency sweep width per unit time, for example, 250 MHz/ 10 msec) and the frequency at the start time (for example, 4000.000 MHz) are previously known, so that the resonance frequency is obtained from the time until when the voltage reaches the peak by the proportional calculation. That is, the frequency sweep of the microwave oscillated from the microwave sweep oscillator is repeated at fixed intervals, and the microwave sweep oscillator simultaneously outputs the sweep signal which becomes a high level only in the sweep. Therefore, the resonance frequency is determined, when the time from when the sweep signal rises until when the transmission intensity becomes the maximum is measured.

The resonance peak level voltage is transmitted to the personal computer 27 through the microcomputer 26, the resonance peak level voltage is compared to the predetermined resonance peak level voltage, the attenuation level of the programmable attenuator is determined according to the deviation (predetermined resonance peak level voltage–current peak level voltage), the attenuation level of the programmable attenuator is changed by outputting the digital signal from the personal computer, and the resonance peak level voltage is adjusted to the predetermined resonance peak level voltage. The personal computer is the control means for comparing the resonance peak level voltage to the predetermined resonance peak level voltage to perform the control based on the difference. In FIG. 20, the above process is performed in each of the five dielectric resonator detection systems by the personal computer.

The predetermined resonance peak level voltage is set as high as possible within the input voltage range of the A/D conversion of the amplifier and A/D conversion circuit units 24a to 24e, although the slight margin is secured so that the input is not saturated. For example, the predetermined resonance peak level voltage is set at 90% of the maximum input voltage. The input voltage to the A/D conversion also depends on magnitude of the pre-stage amplification.

Thus, the measured resonance frequency and resonance peak level voltage are transmitted to the personal computer through the microcomputer 26. The personal computer compares the predetermined target resonance peak level voltage to the actually measured resonance peak level voltage, and the personal computer controls the attenuation level of the programmable attenuator according to the deviation. Briefly, the attenuation level is increased when the peak voltage is larger than the predetermined voltage, and the attenuation level is decreased to enhance the microwave power when the peak voltage is smaller than the predetermined voltage.

The constant resonance peak level voltage is always obtained by automatically and continuously repeating the above control in a short period.

A specific example of the above control will be described below. Assuming that P1 is the measured resonance peak level voltage and P2 is the predetermined target resonance peak level voltage, P is calculated by the following equation.

$$P=10\times\log(P1/P2)$$

Figure 21:
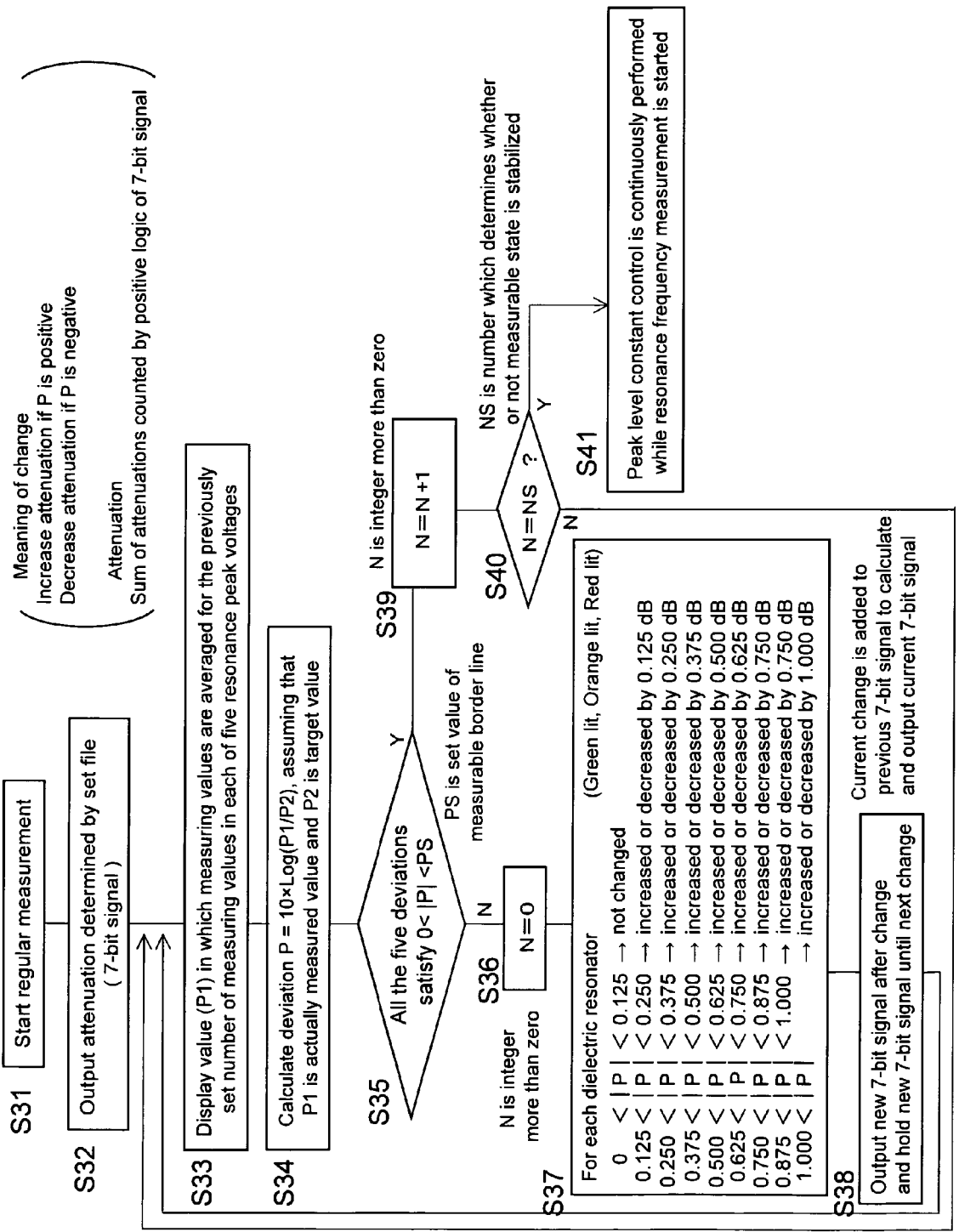
FIG. 21 is a flowchart showing an operation in which an attenuation level is determined in the programmable attenuator.

To what degree the attenuation level of the programmable attenuator is determined when an absolute value of P exists in which range, is determined according to a flowchart shown in FIG. 21 using the personal computer. FIG. 21 is a flowchart showing an operation in which the predetermined target resonance peak level voltage is compared to the actually measured resonance peak level voltage to control the attenuation level of the programmable attenuator according to the deviation. When the measuring data of the new resonance peak level voltage is inputted to the personal computer by performing the control according to the flowchart of FIG. 21, the setting of the attenuation level is changed to always substantially maintain the resonance peak level voltage constant.

The flowchart of FIG. 21 will be briefly described. The regular measurement is started from Step 31. In Step 32, the personal computer outputs the attenuation level to each programmable attenuator. The attenuation level is previously set as an initial value at a setting file in the personal computer. In Step 33, the measuring values are averaged for the previously set number of measuring values in each of the five resonance peak voltages obtained from the five dielectric resonators in this embodiment, and the averaged values are displayed in the personal computer. In Step 34, the deviation is calculated between the target value (target resonance peak level voltage) and the actual measurement value. Assuming that P1 is the actual value and P2 is the target value (P2 is previously set in the setting file), the deviation P is calculated by the following equation.

$$P=10\times\log(P1/P2)$$

In Step 35, it is determined whether or not the deviation P is lower than a certain constant value PS for all the dielectric resonators. The constant value PS is a setting value of a border line in which the measured value is brought close enough to the target value to be able to perform the actual measurement. When the deviation P is not lower than the constant value PS, the flow goes to Step 36 as No, and N is set at zero. In Step 37, the signal is determined for each programmable attenuator according to the deviation for each dielectric resonator. In Step 38, the signal is outputted and held for each programmable attenuator. Then, the flows returns to Step 33. In Step 35, when it is determined that the measurement can be performed because the deviation P is lower than the constant value PS, the flow goes to Step 39 and N is incremented by one. In Step 40, it is determined whether or not N is equal to NS. NS is a predetermined value which determines whether the measurable state is sufficiently stable or not.

In Step 40, when the measurable state is sufficiently stable, namely, when the resonance peak level voltage is substantially maintained constant while sufficiently stabilized, the flow goes to Step 41. In Step 41, the resonance frequency is measured, namely, the orientation measurement is performed. The information on a degree of stability is appropriately displayed in the personal computer by lighting green, orange, and red lamps during the flow of FIG. 21.

When the one-time amount of change in attenuation level of the programmable attenuator is excessively increased, sometimes the fluctuation is further increased to generate the so-called overshoot in a case where the change in attenuation level and the peak voltage overlap each other. Therefore, when the deviation exists within a predetermined range, the stable control can frequently be performed by changing the attenuation level in a unit of the minimum resolution. In a case where the absolute value of P is small, e.g, in a case where the absolute value of P is not more than 0.125, no change is required. To what degree the attenuation level is determined when the absolute value of P exists in which range may be adjusted to the actual measurement system. However, basically the attenuation level is changed by the amount in which the measured value is shifted from the target value.

Figure 22A:
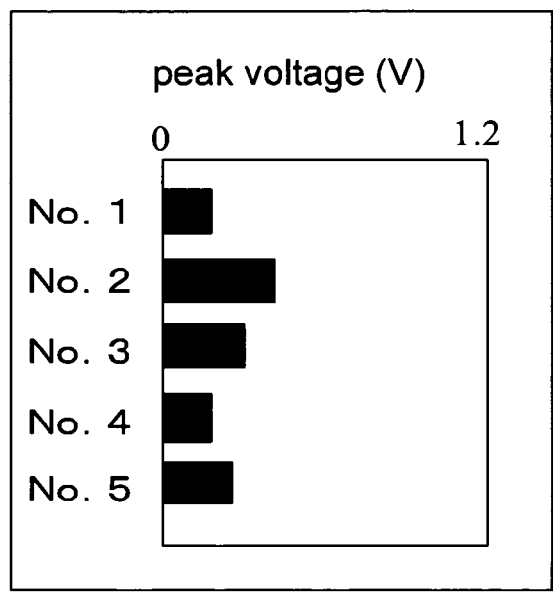
FIG. 22A shows a state immediately after the measurement is started.
Figure 22B:
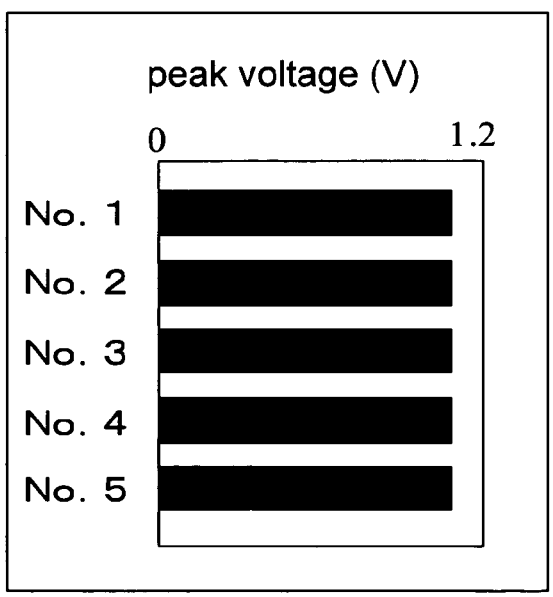
FIG. 22B shows a state after the programmable attenuator is operated.

The actual measurement is performed with the apparatus in which the dielectric resonator circuit of the orientation meter is used as shown in FIG. 20. The settings of the devices are as follows. SM5947 (product of Anritsu Corporation) is used as the microwave sweep oscillator, a sweep width ranges from 3940 to 4190 MHz, the sweep speed is 10 msec, and the target resonance peak voltage is set at 1.1V which is 90% of the maximum input voltage of the A/D conversion by the personal computer. FIG. 22 shows the state in which the output voltage of each dielectric resonator is displayed on the display of the personal computer. FIG. 22A shows the state immediately after the measurement is started, and FIG. 22B shows the state after several seconds elapse since the measurement is started. As can be seen from FIGS. 22A and 22B, even if the resonance peak voltages of the five dielectric resonators are fluctuated immediately after the measurement is started, the resonance peak voltages are equalized to the target resonance peak voltage in 2 to 3 seconds as shown in FIG. 22B.

Figure 23:
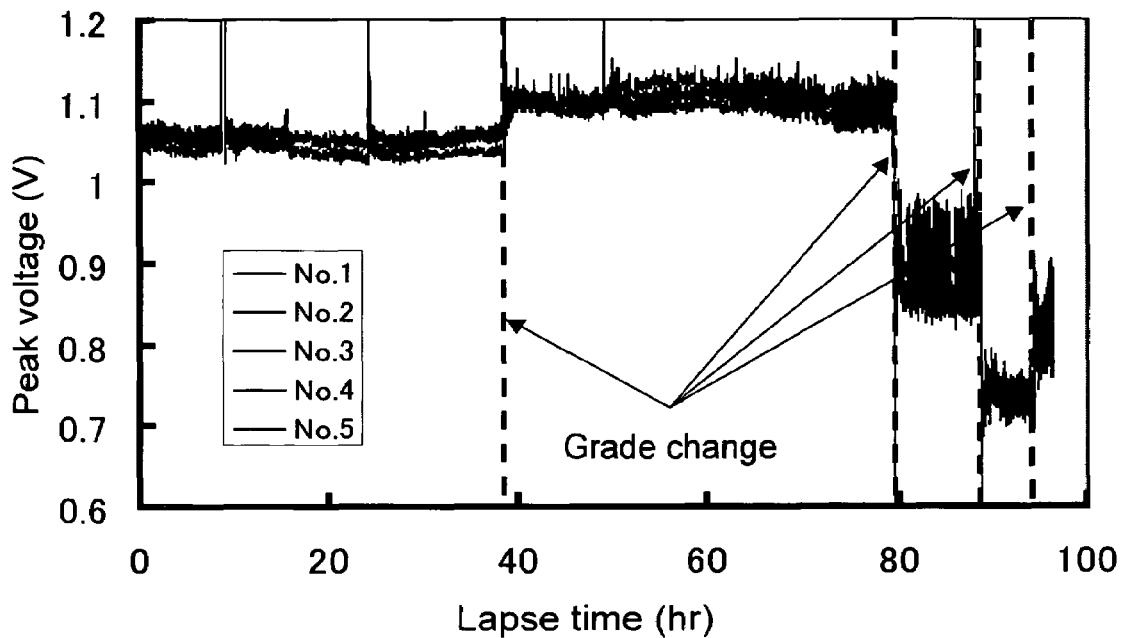
FIG. 23 shows a resonance peak voltage of each dielectric resonator in making a paper sheet when control for maintaining the resonance peak voltage constant is not performed.
Figure 24:
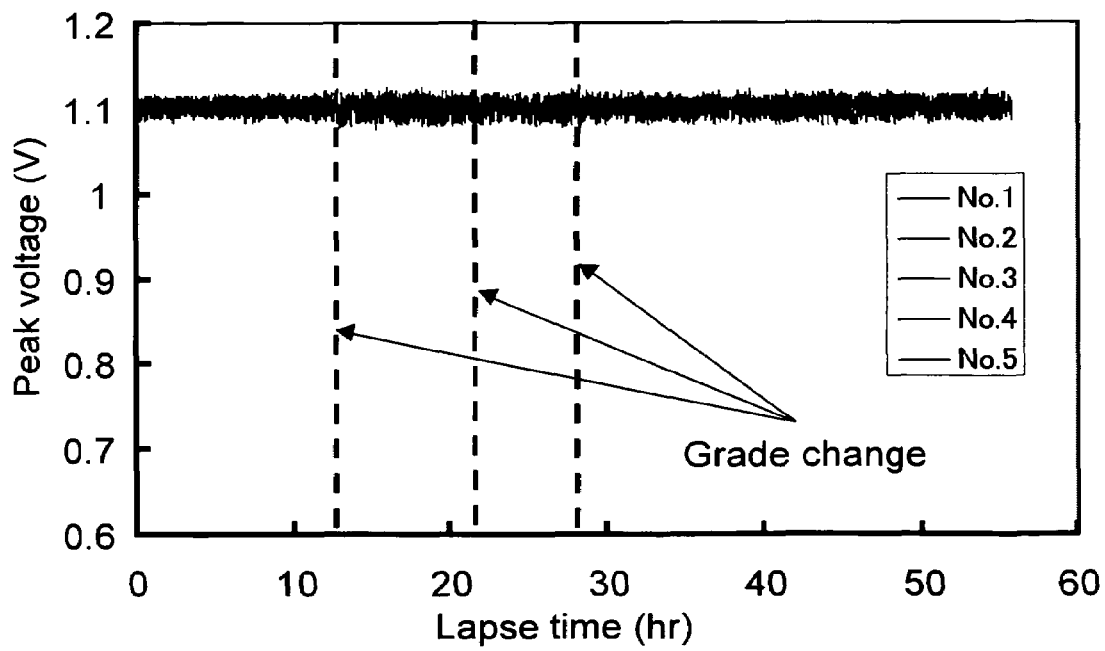
FIG. 24 shows the resonance peak voltage after the control for maintaining the resonance peak voltage of FIG. 23 constant is performed.

FIGS. 23 shows the state of the resonance peak voltage of each dielectric resonator in making the paper sheet as time advances. In FIG. 23, at the time of grade change, a composition, the thickness, and the grammage (weight per unit area) of the paper are changed during the measurement by changing the kind of paper. As shown in FIG. 24, in a case where the control for maintaining the resonance peak voltage constant is performed during the measurement, the five dielectric resonators are maintained at the constant voltage of 1.1V. On the contrary, as shown in FIG. 23, in a case where the control for maintaining the resonance peak voltage constant is not performed, the resonance peak voltage is changed, which changes the resonance frequency. Therefore, the correct orientation pattern is not obtained.

Thus, not only the measurement accuracy of the resonance frequency which is of the final measuring item is improved by maintaining the resonance peak voltage constant, but also the fluctuation in resonance frequency is decreased to improve the stability. For comparison, Table 1 shows standard deviation of the resonance frequency of each of the five dielectric resonators (No. 1 to No. 5) for a case where the control for maintaining the resonance peak voltage constant is performed and the case where the control for maintaining the resonance peak voltage constant is not performed. In a case where the control for maintaining the resonance peak voltage constant is not performed, the standard deviation is 43.45 kHz for the resonance frequency of about 4000 MHz. In a case where the control for maintaining the resonance peak voltage constant is performed, the standard deviation is remarkably decreased to 30.27 kHz for the resonance frequency of about 4000 MHz, and the measurement can stably be performed.

TABLE 1

| | standard deviation (KHz) | | | | | |
|---|---|---|---|---|---|---|
| | No. 1 | No. 2 | No. 3 | No. 4 | No. 5 | Average |
| with control | 28.51 | 34.25 | 34.87 | 27.43 | 26.27 | 30.27 |
| without control | 47.82 | 39.78 | 45.17 | 49.17 | 35.37 | 43.45 |

In a circuit of the embodiment, the data is processed from the middle of the circuit by the digital system. However, the circuit may obviously be formed by all the analog systems, or the circuit may be formed by appropriately using both the analog system and the digital system.

In a case where the control for maintaining the resonance peak voltage constant is performed, the moisture content amount and the like cannot simply be determined based on the difference in resonance peak level between the presence and absence of the sample. In some cases of the invention, the control is performed so that the resonance peak levels are equalized and maintained constant in a case where the sample is present and in a case where the sample is absent In this case, it can be assumed that the difference in resonance peak level is the difference in average value of the attenuation levels between the presence and absence of the sample in the programmable attenuators for the dielectric resonators which is the basis for making the resonance peak level constant.

The invention can be applied to the grammage measurements of sheet-like substances such as paper, non-woven fiber, and film.

What is claimed is:

1. A grammage measuring method for determining a grammage of a measuring sample by arranging a sample measuring surface of a dielectric resonator at only one surface side of a sample under a fixed condition, the grammage measuring method comprising the steps of:
   a first step of obtaining a calibration curve, which indicates a resonance frequency shift amount for a grammage, by measuring a resonance frequency shift amount of the dielectric resonator for each grammage of a standard sample, which has a known grammage, by changing the grammage while a dielectric constant and a density of the standard sample are kept constant;
   a second step of measuring a resonance frequency shift amount of the measuring sample, which has the same dielectric constant and density as the standard sample and has an unknown grammage, under the fixed condition with the dielectric resonator; and
   a third step of determining the grammage of the measuring sample from the measuring value of the second step and the calibration curve,
   where, the resonance frequency shift amount is a difference in resonance frequency between absence and presence of the sample (the standard sample or the measuring sample),
   wherein
   a measuring apparatus including a plurality of dielectric resonators is used, the dielectric resonators being arranged in a same first plane so that electric field vectors of the dielectric resonators having one-directional components in an in-sample second plane parallel to the first plane are different in direction from one another,
   resonance peak levels are detected from amplified signals of outputs from the plurality of dielectric resonators while attenuating or amplifying an output of microwave oscillation means to each of the plurality of dielectric resonators or the outputs from the plurality of dielectric resonators so that each resonance peak level is brought close to a predetermined resonance peak level, dielectric anisotropy of the measuring sample is determined from a difference in output among the plurality of dielectric resonators, and the calibration curve is determined using an average value of the outputs of the plurality of dielectric resonators, and the grammage of the measuring sample is determined from the calibration curve and measurement result based on the average value of the outputs of the plurality of dielectric resonators for the measuring sample.

2. A grammage measuring method according to claim 1, wherein the fixed condition is performance of the measurement by bringing the sample into contact with the sample measuring surface of the dielectric resonator.

3. A grammage measuring method according to claim 1, wherein the fixed condition is performance of the measurement by separating the sample away from the sample measuring surface of the dielectric resonator by a predetermined distance.

4. A grammage measuring method according to claim 1, wherein a moisture content amount or a moisture content ratio of the measuring sample is also determined based on a difference in resonance peak level between the absence and presence of the measuring sample.

5. A grammage measuring method according to claim 1 wherein a moisture content amount or a moisture content ratio of the measuring sample is determined using the average value of the outputs of the plurality of dielectric resonators as the resonance peak level.

6. A grammage measuring method for determining a grammage of a measuring sample by arranging a sample measuring surface of a dielectric resonator at only one surface side of a sample under a fixed condition, the grammage measuring method comprising:

a step of calculating a constant "A" according to the following equation (1) by measuring a resonance frequency shift amount Δf of a standard sample, which has a known grammage "b", under the fixed condition; and a step of calculating a grammage "b" of the measuring sample, which has the same dielectric constant and density as the standard sample, according to the following equation (1) by measuring a resonance frequency shift amount Δf of the measuring sample under the fixed condition with the dielectric resonator:

$$\Delta f = A \cdot b \quad (1)$$

where, $\Delta f = f_0 - f_S$, $f_0$: a resonance frequency in a case where the sample (the standard sample or the measuring sample) is absent, and $f_S$: a resonance frequency in a case where the sample (the standard sample or the measuring sample) is present, wherein a measuring apparatus including a plurality of dielectric resonators is used, the dielectric resonators being arranged in a same first plane so that electric field vectors of the dielectric resonators having one-directional components in an in-sample second plane parallel to the first plane are different in direction from one another, resonance peak levels are detected from amplified signals of outputs from the plurality of dielectric resonators while attenuating or amplifying an output of microwave oscillation means to each of the plurality of dielectric resonators or the outputs from the plurality of dielectric resonators so that each resonance peak level is brought close to a predetermined resonance peak level, dielectric anisotropy of the measuring sample is determined from a difference in output among the plurality of dielectric resonators, and the constant "A" is determined using an average value of the outputs of the plurality of dielectric resonators, and the grammage of the measuring sample is determined from the constant "A" and measurement result based on the average value of the outputs of the plurality of dielectric resonators for the measuring sample.

7. A grammage measuring method according to claim 6, wherein the fixed condition is performance of the measurement by bringing the sample into contact with the sample measuring surface of the dielectric resonator.

8. A grammage measuring method according to claim 6, wherein the fixed condition is performance of the measurement by separating the sample away from the sample measuring surface of the dielectric resonator by a predetermined distance.

9. A grammage measuring method according to claim 6, wherein a moisture content amount or a moisture content ratio of the measuring sample is also determined based on a difference in resonance peak level between the absence and presence of the measuring sample.

10. A grammage measuring method according to claim 6, wherein a moisture content amount or a moisture content ratio of the measuring sample is determined using the average value of the outputs of the plurality of dielectric resonators as the resonance peak level.

11. A grammage measuring apparatus comprising:

a dielectric resonator being arranged at only one surface side of a measuring sample;

a shielding container substantially covering the dielectric resonator except for a sample measuring surface;

a microwave excitation device for causing the dielectric resonator to generate an electric field vector;

a detection device for detecting transmission energy or reflection energy by the dielectric resonator;

a storage device storing a calibration curve, which indicates a resonance frequency shift amount for a grammage and is produced based on a resonance frequency shift amount of the dielectric resonator for each grammage of a standard sample, which has a known grammage, by changing the grammage while a dielectric constant and density of the standard sample are kept constant; and a data processing device for determining a grammage of a measuring sample from the resonance frequency shift amount of the measuring sample, which has the same dielectric constant and density as the standard sample, and the calibration curve, wherein, the resonance frequency shift amount is the difference in resonance frequency between absence and presence of the sample (the standard sample or the measuring sample), wherein the dielectric resonator includes a plurality of dielectric resonators arranged on a same first plane so that electric field vectors of the dielectric resonators having one-directional components in an in-sample second plane parallel to the first plane are different in direction from one another, the data processing device has a function of determining a dielectric anisotropy of the measuring sample based on a difference in output among the dielectric resonators, and thereby the grammage measuring apparatus has an orientation measuring function, and the calibration curve is determined using an average value of the outputs of the plurality of dielectric resonators, and the grammage of the measuring sample is determined from the calibration curve and measurement result based on the average value of the outputs of the plurality of dielectric resonators for the measuring sample, an amplifier circuit includes a time delay element, the amplifier circuit being connected to each of the plurality of dielectric resonators to amplify output of each of the plurality of dielectric resonators, each of the plurality of dielectric resonators constitutes a dielectric resonator detection system including a variable electric signal attenuation and amplification means, the variable electric signal attenuation and amplification means being inserted between a microwave oscillator and a resonance peak level detection circuit, the microwave oscillator being connected to each of the plurality of dielectric resonators, the resonance peak level detection circuit being connected to the amplifier circuit to detect a resonance peak level from the output of the amplifier circuit, and the grammage measuring apparatus includes control means for comparing the output from the resonance peak level detection circuit of each dielectric resonator detection system to a predetermined resonance peak level to generate a signal for changing an attenuation or an amplification degree for the variable electric signal attenuation and amplification means so that the output from the resonance peak level detection circuit is brought close to the predetermined resonance peak level.

12. A grammage measuring apparatus according to claim 11, wherein the data processing device has a function of determining a moisture content amount or a moisture content ratio of the measuring sample based on the difference in resonance peak level between the absence and presence of the measuring sample, and thereby the grammage measuring apparatus has a moisture measuring function.

13. A grammage measuring apparatus according to claim 11, wherein the dielectric resonator includes a single dielectric resonator having a one-directional component in an in-sample plane, the grammage measuring apparatus has a rotating mechanism which rotates the sample or the dielectric resonator on the plane;

the data processing device has a function of determining a dielectric anisotropy of the measuring sample from the difference in dielectric resonator output according to the rotation of the rotating mechanism, and thereby the grammage measuring apparatus has an orientation measuring function, and the grammage measuring apparatus determines the calibration curve by using an average value of the dielectric resonator outputs according to the rotation of the rotating mechanism, and obtains the grammage of the measuring sample from the calibration curve and the measurement result based on the average value of the dielectric resonator outputs for the measuring sample.

14. A grammage measuring apparatus comprising:

a dielectric resonator being arranged only at one surface side of a measuring sample;

a shielding container substantially covering the dielectric resonator except for a sample measuring surface;

a microwave excitation device for causing the dielectric resonator to generate an electric field vector;

a detection device for detecting transmission energy or reflection energy by the dielectric resonator;

a storage device storing a constant "A" according to the following equation (2), the constant "A" being determined based on a resonance frequency shift amount Δf for each grammage of a standard sample, which has a known grammage "b", measured under the fixed condition with the dielectric resonator by changing the grammage while a dielectric constant and a density of the standard sample are kept constant; and a data processing device for calculating a grammage "b" of the measuring sample, which has the same dielectric constant and density as the standard sample, according to the following equation (2) from the constant A stored in the storage device and a measurement result of a resonance frequency shift amount Δf of the measuring sample under the fixed condition with the dielectric resonator:

$$\Delta f = A \cdot b \qquad (1)$$

where, $\Delta f = f_0 - f_S$, $f_0$: a resonance frequency in a case where the sample (the standard sample or the measuring sample) is absent, and $f_S$: a resonance frequency in a case where the sample (the standard sample or the measuring sample) is present, wherein the dielectric resonator includes a plurality of dielectric resonators arranged on a same first plane so that electric field vectors of the dielectric resonators having one-directional components in an in-sample second plane parallel to the first plane are different in direction from one another, the data processing device has a function of determining a dielectric anisotropy of the measuring sample based on a difference in output among the dielectric resonators, and thereby the grammage measuring apparatus has an orientation measuring function, the constant "A" is determined using an average value of the outputs of the plurality of dielectric resonators, and the grammage of the measuring sample is determined from the constant "A" and measurement result based on the average value of the outputs of the plurality of dielectric resonators for the measuring sample, an amplifier circuit includes a time delay element, the amplifier circuit being connected to each of the plurality of dielectric resonators to amplify an output of each of the plurality of dielectric resonators, each of the plurality of dielectric resonators constitutes a dielectric resonator detection system including a variable electric signal attenuation and amplification means, the variable electric signal attenuation and amplification means being inserted between a microwave oscillator and a resonance peak level detection circuit, the microwave oscillator being connected to each of the plurality of dielectric resonators, the resonance peak level detection circuit being connected to the amplifier circuit to detect a resonance peak level from the output of the amplifier circuit, and the grammage measuring apparatus includes control means for comparing the output from the resonance peak level detection circuit of each dielectric resonator detection system to a predetermined resonance peak level to generate a signal for changing an attenuation or an amplification degree for the variable electric signal attenuation and amplification means so that the output from the resonance peak level detection circuit is brought close to the predetermined resonance peak level.

15. A grammage measuring apparatus according to claim 14, wherein the data processing device has a function of determining a moisture content amount or a moisture content ratio of the measuring sample based on the difference in resonance peak level between the absence and presence of the measuring sample, and thereby the grammage measuring apparatus has a moisture measuring function.

16. A grammage measuring apparatus according to claim 14, wherein the dielectric resonator includes a single dielectric resonator having a one-directional component in an in-sample plane, the grammage measuring apparatus has a rotating mechanism which rotates the sample or the dielectric resonator on the plane;

the data processing device has a function of determining a dielectric anisotropy of the measuring sample from the difference in dielectric resonator output according to the rotation of the rotating mechanism, and thereby the grammage measuring apparatus has an orientation measuring function, and the grammage measuring apparatus determines the calibration curve or the constant "A" by using an average value of the dielectric resonator outputs according to the rotation of the rotating mechanism, and obtains the grammage of the measuring sample from the calibration curve or the constant "A" and the measurement result based on the average value of the dielectric resonator outputs for the measuring sample.

* * * * *